United States Patent
Brewer et al.

(10) Patent No.: US 7,448,109 B2
(45) Date of Patent: *Nov. 11, 2008

(54) ORAL HYGIENE DEVICES

(75) Inventors: Gerald K. Brewer, Redmond, WA (US); James Christopher McInnes, Seattle, WA (US); Daniel Bayeh, Seattle, WA (US); Frederick Jay Bennett, Kirkland, WA (US); Richard K. Taylor, Fall City, WA (US); David A. Ballard, Sammamish, WA (US); George A. Barrett, Shoreline, WA (US)

(73) Assignee: Ultreo, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/613,994

(22) Filed: Dec. 20, 2006

(65) Prior Publication Data
US 2007/0079455 A1    Apr. 12, 2007

Related U.S. Application Data

(63) Continuation of application No. 11/416,723, filed on May 3, 2006.

(60) Provisional application No. 60/677,577, filed on May 3, 2005.

(51) Int. Cl.
*A61C 17/22* (2006.01)

(52) U.S. Cl. .................. 15/22.1; 433/119; 601/142

(58) Field of Classification Search .......... 15/22.1; 433/118, 119; 601/142
See application file for complete search history.

(56) References Cited

U.S. PATENT DOCUMENTS

| | | |
|---|---|---|
| 3,828,770 A | 8/1974 | Kuris et al. |
| 5,305,492 A | 4/1994 | Giuliani et al. |
| 5,311,632 A | 5/1994 | Center |

(Continued)

FOREIGN PATENT DOCUMENTS

JP    2003-61986    *  3/2003

(Continued)

OTHER PUBLICATIONS

McInnes, Christopher et al., "Designing the Next Generation of a Sonic Toothbrush," Am. J. Dent., vol. 15, pp. 4B-6B (Nov. 2002).

(Continued)

*Primary Examiner*—Mark Spisich
(74) *Attorney, Agent, or Firm*—Ann W. Speckman; Speckman Law Group PLLC

(57) ABSTRACT

An oral hygiene device having an ultrasound transducer 22 and an acoustic waveguide 24 facilitating the transmission of ultrasonic acoustic energy to fluids in the oral cavity is disclosed. Preferred ultrasound operating parameters for operation in aqueous environments and in dental slurries are disclosed. Devices may incorporate a drive motor 16 for oscillating a device head 23, acoustic waveguide 24 and one or more bristle tuft(s) 26 at sonic frequencies, and preferred sonic operating parameters are also provided. Multi-element piezoelectric transducer assemblies 30, 40, and various control and communications features are disclosed. Oral hygiene devices disclosed herein achieve improved plaque and stain removal from the teeth as well as interproximal and subgingival regions, while enhancing the user experience, massaging the gums, stimulating dental tissue, and disrupting biofilm.

34 Claims, 4 Drawing Sheets

U.S. PATENT DOCUMENTS

| | | | |
|---|---|---|---|
| 5,378,153 | A | 1/1995 | Giuliani et al. |
| 5,546,624 | A | 8/1996 | Bock |
| 5,827,064 | A | 10/1998 | Bock |
| 5,938,612 | A | 8/1999 | Kline-Schoder et al. |
| 6,446,295 | B1 | 9/2002 | Calabrese |
| 6,735,802 | B1 | 5/2004 | Lundell et al. |
| 6,821,119 | B2 | 11/2004 | Shortt et al. |
| 2003/0115694 | A1 | 6/2003 | Pace |
| 2004/0255409 | A1 | 12/2004 | Hilscher et al. |
| 2005/0091770 | A1 | 5/2005 | Mourad et al. |
| 2005/0241666 | A1 | 11/2005 | Bodet et al. |
| 2005/0283928 | A1 | 12/2005 | Grez et al. |
| 2006/0191086 | A1 | 8/2006 | Mourad et al. |

FOREIGN PATENT DOCUMENTS

| | | | |
|---|---|---|---|
| JP | 2003-88426 | * | 3/2003 |
| JP | 2003-180717 | * | 7/2003 |
| JP | 2004-148079 A | | 5/2004 |
| JP | 2004-202065 | * | 7/2004 |
| JP | 2004-202065 A | | 7/2004 |
| JP | 2005-34312 | * | 2/2005 |
| RU | 506421 | | 3/1978 |

OTHER PUBLICATIONS

Hope, Christopher K. et al., "Comparison of the Interproximal Plaque Efficacy of Two Powered Toothbrushes Using In Vitro Oral Biofilms," Am. J. Dent., vol. 15, pp. 7B-11B (Nov. 2002).

McInnes, C. et al., "Fimbria Damage and Removal of Adherent Bacteria After Exposure to Acoustic Energy," Oral Microbiol. Immunol., vol. 8, pp. 277-282 (1993).

McInnes, C. et al., "Reduction in Adherence of Actinomyces Viscosus After Exposure to Low-Frequency Acoustic Energy," Oral Microbiol. Immunol., vol. 7, pp. 171-176 (1992).

* cited by examiner

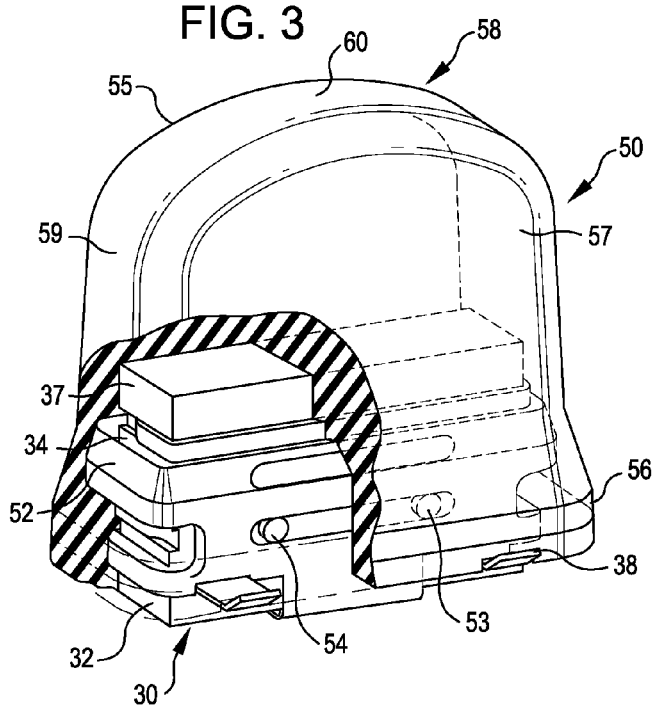
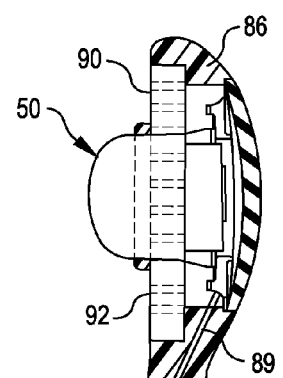
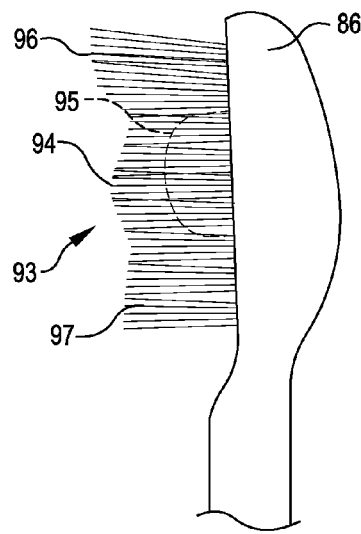
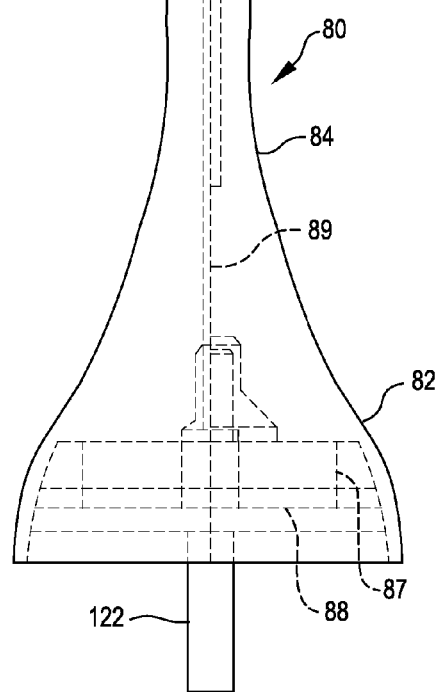

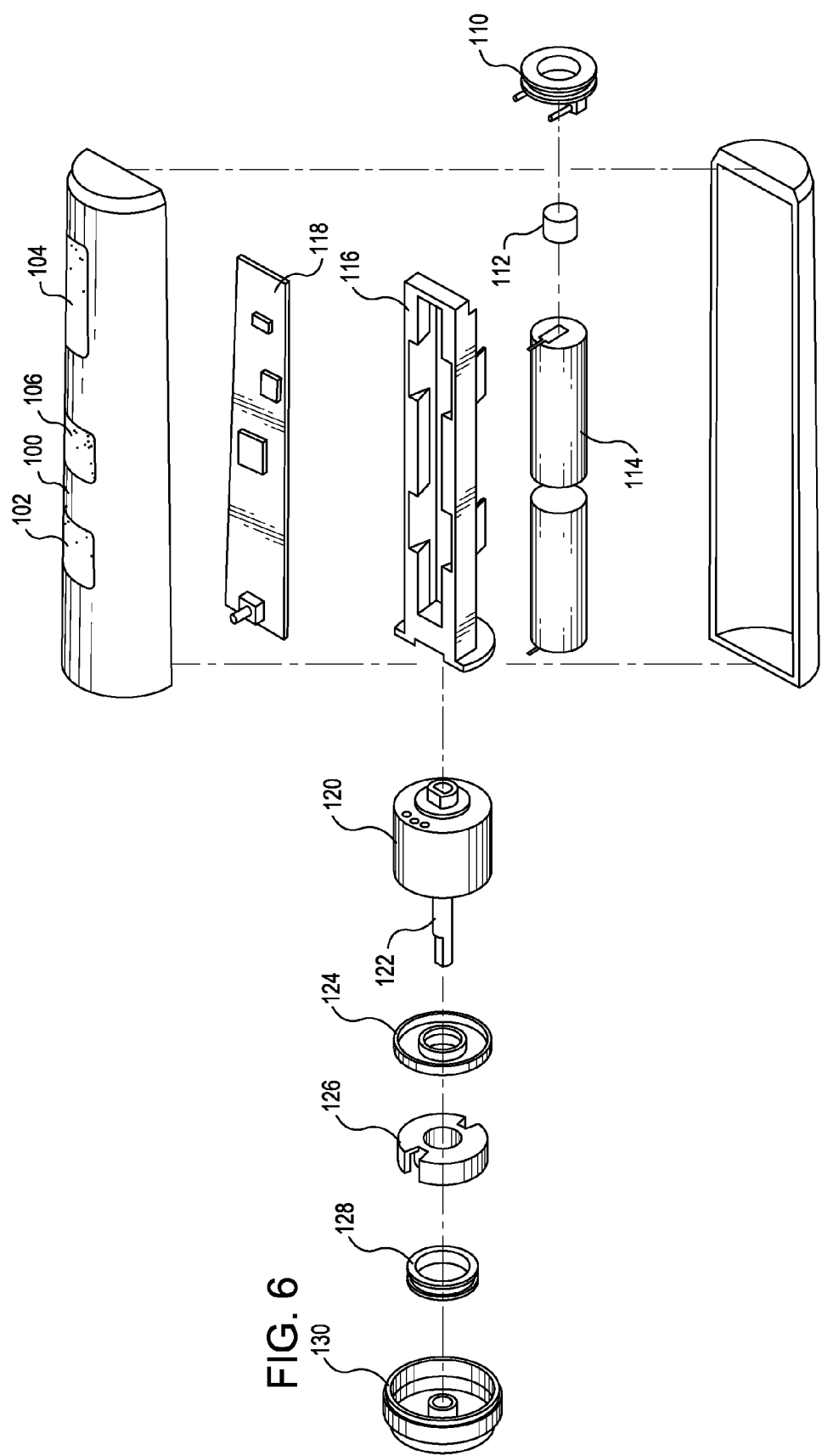

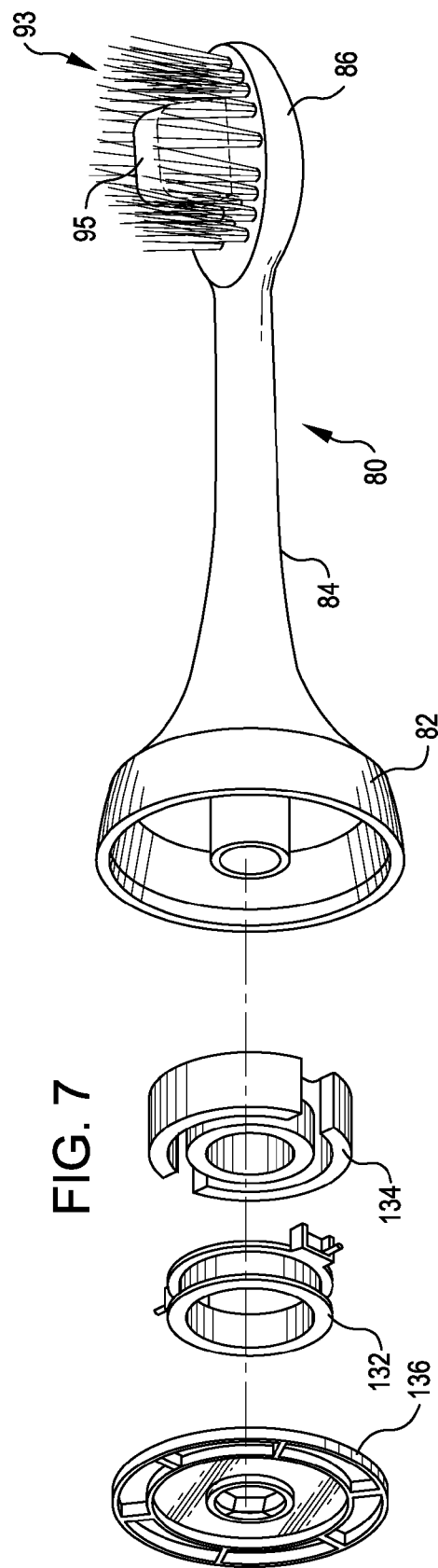

ORAL HYGIENE DEVICES

CROSS-REFERENCE TO RELATED APPLICATIONS

This application is a continuation of U.S. patent application Ser. No. 11/416,723, filed May 3, 2006, which claims priority to U.S. Provisional Patent Application No. 60/677,577, filed May 3, 2005.

REFERENCE TO GOVERNMENT SUPPORT

One or more of the inventions disclosed herein were made with Government support under SBIR Contract No. 1-R43-DEO16761-01. The Government may have certain rights in one or more of those inventions.

BACKGROUND OF THE INVENTION

1. Technical Field of the Invention

The present invention relates generally to the field of oral hygiene devices and, more specifically, to the field of oral hygiene devices such as toothbrushes that employ sonic and/or ultrasonic acoustic mechanisms.

2. Brief Description of the Related Art

Even the most effective existing power toothbrushes leave clinically significant plaque at tooth-to-tooth contact surfaces, at the gingival-tooth contact points, below the gingiva and beyond the direct reach of the bristles or other toothbrush components. Many oral hygiene devices employing sonic and/or ultrasonic mechanisms are known in the art. Previous attempts to take advantage of ultrasound acoustic energy in toothbrushes failed to exploit microbubble formation in dental fluid for purposes of facilitating plaque removal, or failed to consider microbubbles and macrobubbles as a potential impediment to ultrasound propagation beyond the bristle tips.

Some toothbrushes that employed ultrasound technology attempted to achieve the propagation of ultrasound waves from the base of the bristles either through the bristles themselves or through the bubbly dental fluid that fills the spaces between the bristles. For example, U.S. Pat. Nos. 5,138,733 and 5,546,624 to Bock disclose an ultrasonic toothbrush having a handle, a battery pack, an electronics driving module, a piezoelectric member, and a removable brush head. U.S. Pat. Nos. 5,247,716 and 5,369,831 to Bock disclose a removable brush head for an ultrasonic toothbrush having a plurality of bristle clusters, a substantially tubular body constructed of a flexible material, and tensioning means securing the brush head to the ultrasonic device, providing for the efficient transmission of ultrasonic frequency oscillations from the device via the brush head. Because conventional toothbrush bristles and bubbly dental fluid can reduce rather than facilitate the propagation of ultrasound waves, the toothbrushes disclosed in these references would not achieve efficient ultrasound wave propagation. Also, the ultrasound systems in prior art toothbrushes did not take advantage of the specific bubble structure within dental fluid.

U.S. Pat. No. 3,335,443 to Parisi discloses a brush that is coupled to an ultrasonic, vibratory handheld dental instrument that is capable of being oscillated at high sonic and ultrasonic frequencies. U.S. Pat. No. 4,071,956 to Andress discloses a device that is not a toothbrush, for removing dental plaque by ultrasonic oscillations.

U.S. Pat. No. 3,809,977 to Balamuth et al., which reissued as U.S. Pat. No. RE 28,752, discloses ultrasonic kits, ultrasonic motor constructions, and ultrasonic converter designs for use alone or in combination. The ultrasonic motor may be of piezoelectric material having a removable tip and is contained in a housing having an electrical contact means adapted to be plugged into an adapter that is connected to a converter. U.S. Pat. No. 3,840,932 and No. 3,941,424 to Balamuth et al. disclose an ultrasonic toothbrush applicator in a configuration to be ultrasonically oscillated to transmit mechanical oscillations from one end to a bristle element positioned at the other end.

U.S. Pat. No. 3,828,770 to Kuris et al. discloses a method for cleaning teeth employing bursts of ultrasonic mechanical oscillation at an applicator repeated at a sonic frequency to produce both ultrasonic and sonic vibratory motion during use.

U.S. Pat. No. 4,192,035 to Kuris discloses an apparatus comprising an elongated member formed of a piezoelectric member with a pair of contacting surfaces with a brush member adapted to be received within the mouth. A casing adapted into a handle is configured to receive the piezoelectric member. U.S. Pat. No. 4,333,197 to Kuris discloses an ultrasonic toothbrush that includes an elongated handle member in the form of a hollow housing having a low voltage coil and cooperating ferrite core that is driven at ultrasonic frequencies. A brush member is affixed to the core and is adhesively affixed to an impedance transfer device that is adhesively affixed to the core material. The impedance transfer device insures maximum transfer of ultrasonic energy from the core material to the brush.

U.S. Pat. No. 4,991,249 and No. 5,150,492 to Suroff disclose an ultrasonic toothbrush having an exchangeable toothbrush member that is removably attached to an ultrasonic power member.

U.S. Pat. No. 5,311,632 to Center discloses a device for removing plaque from teeth comprising a toothbrush having a thick, cylindrical, hollow handle encompassing an electric motor that is actuable to cause rotation of an eccentrically mounted member and oscillation of the entire device and an ultrasonic transducer actuable to produce high frequency sound waves along the brush.

Japan Application No. P1996-358359, Pat. Laid Open 1998-165228, discloses a toothbrush utilizing ultrasonic waves in which an ultrasonic wave generator is provided in the handle of a manual or electrically powered toothbrush and an ultrasonic wave vibrator is mounted in the brush and wired to the wave generator.

Japan Application No. P2002-353110, Pat. Laid Open 2004-148079, discloses an ultrasonic toothbrush wherein ultrasonic oscillation is radiated from a piezoelectric vibrator arranged inside a brush head and transmitted to the teeth via a rubber projection group.

U.S. Pat. No. 6,203,320 to Williams et al. discloses an electrically operated toothbrush and method for cleaning teeth. The toothbrush includes a handle, a brush head connected to the handle having a plurality of hollow filament bristles, passageways through the handle and brush head for transporting fluid into and through the hollow filament bristles, an electrical energy source in the handle, and a vibratory element for imparting a pulsation to the fluid being transported.

U.S. Patent Publication No. 2003/0079305 to Takahata et al. discloses an electric toothbrush in which a brush body is simultaneously oscillated and reciprocated. The electric toothbrush comprises a casing main body, an arm extending above the casing main body, a brush body arranged in a top end of the arm, and an ultrasonic motor arranged in a top end inside of the arm for driving the brush body.

U.S. Pat. No. RE 35,712, which is a reissue of U.S. Pat. No. 5,343,883 to Murayama, discloses an electric device (i.e. a flosser) for removal of plaque from interproximal surfaces. The device employs sonic energy and dental floss secured between two tines of a flexible fork removably attached to a powered handle. The electric motor revolves at sonic frequencies to generate sonic energy that is transmitted to the flexible fork.

U.S. Pat. No. 6,619,957 to Mosch et al. discloses an ultrasonic scaler comprising a scaler tip, actuator material, a coil, a handpiece housing, and an air-driven electrical current generator. The actuator material, coil, and air-driven electrical current generator are all encompassed within the handpiece housing.

U.S. Pat. No. 6,190,167 to Sharp discloses an ultrasonic dental scaler for use with a dental scaler insert having a resonant frequency. The dental scaler insert is removably attached to a handpiece having an energizing coil coupled to a selectively tunable oscillator circuit to generate a control signal having an oscillation frequency for vibrating the dental scaler.

U.S. Pat. No. 4,731,019 to Martin discloses a dental instrument for scaling by ultrasonic operation. The instrument of the dental instrument has a distal end with a hook-like configuration with a conical pointed end and comprising abrasive particles, typically diamond particles.

U.S. Pat. No. 5,378,153 to Giuliani discloses a dental hygiene apparatus having a body portion and an extended resonator arm. The apparatus employs an electromagnet in its body that acts in combination with two permanent magnets to achieve an oscillating action about a torsion pin. The arm is driven such that the bristle-tips operate within ranges of amplitude and frequency to produce a bristle tip velocity greater than 1.5 meters per second to achieve cleansing beyond the tips of the bristles.

U.S. Patent Publication No. 2005/0091770 A1 discloses a toothbrush employing an acoustic waveguide that facilitates the transmission of acoustic energy into the dental fluid. The acoustic waveguide may be used in combination with a sonic component and/or an ultrasonic transducer. The disclosure of this publication is incorporated herein by reference in its entirety.

There remains a need in the art for devices that provide improved oral hygiene, and particularly that improve cleaning between the teeth and gums, at points of contact between the teeth, and beyond the direct action of the bristles.

SUMMARY OF THE INVENTION

Oral hygiene devices having an acoustic waveguide, an ultrasound transducer assembly and/or a drive motor for generating oscillations at sonic frequencies are provided herein. The device head typically comprises a support structure having an acoustic waveguide, an ultrasound transducer assembly, and one or more bristle tufts mounted therein. A handle structure typically houses a rechargeable power supply, a motor generating oscillations at sonic frequencies, an ultrasound drive circuit, and a controller. The device head may be detachably mounted to the handle and replaceable. The device may also include a battery charging station that is connectable to an external power supply for recharging the batteries. A user interface comprising at least an on/off control is provided and, upon activation of the device by the user, an operating cycle is initiated. Suitable ultrasound operating parameters and sonic oscillating parameters and protocols are described in detail below.

Within various embodiments, the present invention provides oral hygiene devices, such as toothbrushes, including manual (non-motorized) toothbrushes incorporating an ultrasound transducer and an acoustic waveguide structure, power (motorized) toothbrushes incorporating an acoustic waveguide structure, and power (motorized) toothbrushes incorporating both an ultrasound transducer and an acoustic waveguide structure. The acoustic waveguide structure, in combination with an ultrasound transducer and/or motor for generating oscillation at sonic frequencies, and optionally in combination with one or more bristle tufts, acts upon the microscopic bubbly flow within fluid in the operating environment to induce cavitation, acoustic streaming and/or acoustic microstreaming within the fluid. Oscillation of the brush head at sonic frequencies, in combination with emission of acoustic energy from the acoustic waveguide at ultrasound frequencies, and/or in combination with the oscillation of one or more bristle tufts, furthermore generates a favorable mouth feel, stimulates and massages the gums and other dental tissue and, in general, provides an improved dental cleaning experience.

An oral hygiene device such as a toothbrush, employing an acoustic waveguide in combination with an ultrasound transducer and/or a motor generating oscillations at sonic frequencies under the conditions described herein, provides improved cleaning properties and disruption of biofilm. As described in detail herein, oral hygiene devices according to the present invention are effective in increasing bubbly fluid flow by motion, including sonic motion, of the acoustic waveguide and promoting bubble formation by movement of the waveguide and/or one or more bristle tufts. Oscillation of the brush head at sonic frequencies moves and activates the bristle tips so that they cleanse tooth surfaces by means of direct bristle contact and also generates bubbles within the dental fluid surrounding the waveguide that, when exposed to acoustic energy at ultrasound frequencies, provide improved plaque and biofilm removal.

In embodiments employing an ultrasound transducer, devices of the present invention are effective in transmitting ultrasound waves generated by the ultrasound transducer and propagating those waves through an acoustic waveguide into the oral cavity and the dental fluid to achieve improved plaque disruption and removal, as well as biofilm reduction. Devices of the present invention employing an ultrasound transducer operating in accordance with the parameters described herein in combination with a sonic component are also effective in facilitating bubbly fluid flow and transmitting ultrasound to produce cleaning effects at and beyond the bristles, e.g., from about 0.5 mm to about 7 mm beyond the bristle tips, more typically at least about 1 mm and up to about 5 mm beyond the bristle tips.

Oscillation of bristle tufts and an acoustic waveguide at sonic frequencies generates bubbly flow and improves cleaning, even absent the action of an ultrasound transducer and transmission of acoustic energy through the acoustic waveguide at ultrasound frequencies. It is, however, the combination of the ultrasonic transducer, acoustic waveguide, and sonic component that together achieve the most effective power toothbrush embodiment of the present invention and yield synergistic cleaning effects that are substantially superior to the additive effects of the sonic and ultrasonic components in isolation.

BRIEF DESCRIPTION OF THE DRAWINGS

Various aspects and advantages of this invention will become more readily appreciated and may be better understood by reference to the following detailed description, taken in conjunction with the accompanying drawings, wherein:

FIG. 3 is an enlarged perspective schematic view, partially broken away, illustrating an ultrasound module of the present invention incorporating an ultrasound transducer assembly with an associated matching layer and electrical contacts mounted in a support structure with an acoustic waveguide mounted over and around the transducer assembly;

FIG. 4 shows an enlarged side cross-sectional view of a brush head assembly of the present invention incorporating an ultrasound module and electrodes providing power to the transducer assembly but omitting bristle tufts;

FIG. 5 shows an enlarged side view of a brush head of the present invention having a plurality of bristle tufts;

FIG. 6 shows an exploded view of a device handle and the components typically mounted in the handle; and FIG. 7 shows an enlarged exploded view of a device head and the components typically mounted in the head.

DETAILED DESCRIPTION OF THE INVENTION

Figure 1:
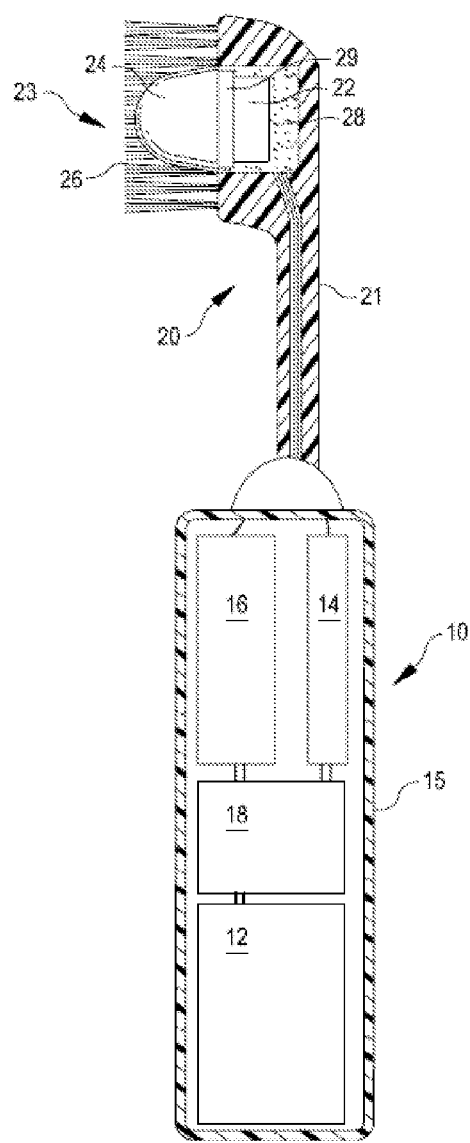
FIG. 1 is a schematic, partially cross sectional diagram depicting an exemplary toothbrush of the present invention incorporating an acoustic waveguide, a plurality of bristle tufts, an ultrasound transducer, and a motor for producing oscillation at sonic frequencies.

As used herein, the terms "ultrasound" and "ultrasonic" refer to acoustic energy having a frequency greater than the normal audible range of the human ear—generally a frequency greater than approximately 20 kHz. The term "sonic" refers to acoustic energy, or sound, having a frequency that is within the normal audible range of the human ear—generally less than about 20 kHZ—for example, between 20 Hz and 20 kHz.

As used herein, the term "cavitation" refers to the generation and/or stimulation of bubbles by sound. By "generation" is meant the creation of bubbles; by "stimulation" is meant the action that causes the bubbles to become dynamically active—that is, to move, to get bigger or smaller, to grow, to dissipate, all with associated mechanical and/or chemical effects in and around the fluid surrounding the bubbles and within the gas inside the bubbles. The term "cavitation" refers to the interaction between an ultrasonic field in a liquid and in gaseous inclusions (e.g., microbubbles) within the insonated medium.

Cavitation of existing microbubbles may be subdivided, to a first approximation, into two general categories—"stable cavitation" and "inertial cavitation." "Stable cavitation" is the induction of stable, low-amplitude, resonant oscillations of preexisting microbubbles by low-intensity ultrasound energy, which, in turn generates local shear forces within the fluid flow (referred to herein as acoustic microstreaming) near and adjacent to the microbubbles. As the ultrasound intensity is increased, the amplitude of oscillation also increases until the bubble becomes unstable and collapses due to the inertia of the inrushing fluid, giving rise to "inertial cavitation." Generally, microbubbles that undergo cavitation under the ultrasonic conditions used in devices of the present invention are between about 1 μm and about 150 μm in diameter. Clusters of microbubbles may also be induced to cavitate.

Oral hygiene devices of the present invention incorporating an ultrasound transducer and an acoustic waveguide typically promote at least stable cavitation—that is, simple volumetric changes in bubbles, where factors in addition to and/or instead of the inertia in the surrounding fluid govern the bubble behavior. Low levels of ultrasonic acoustic energy induce temporal variations in bubble volume, both within an acoustic cycle and over many acoustic cycles, that generate movement within the fluid in proximity to the bubble, whose mechanical effects promote removal of plaque and disruption of biofilm.

"Microbubbles" refer to microscopic bubbles present in the oral cavity, for example, in the dental fluid or plaque. Microbubbles may be endogenous to the fluid—that is, they may be introduced, such as in a fluid or dentifrice containing microbubbles; they may be generated by the movement of toothbrush bristles during manual brushing; and/or they may be generated by the oscillation of bristles and/or an acoustic waveguide at sonic frequencies. "Microbubbles" are acted upon by acoustic energy at ultrasound frequencies transmitted by an ultrasonic transducer and propagated by an acoustic waveguide. "Microbubbles" resonate at or near a specific frequency depending upon the microbubbles' diameter.

"Acoustic streaming" refers to the bulk or coherent flow of fluid that occurs due to momentum transfer from an acoustic wave to a fluid as a result of attenuation of an ultrasound beam. Ultrasound propagating into fluid, with or without bubbles, can generate "acoustic streaming," which can be quite significant in size and extent. Acoustic streaming effects may be even greater with bubbles than without bubbles in a fluid. Acoustic streaming generally requires higher frequencies than are required for stimulating the bubbles and, in general, the higher the ultrasonic frequency, the greater the acoustic streaming effect.

"Microstreaming" and "acoustic microstreaming" refer to the movement of fluid near and adjacent to microbubbles that occurs as a result of the action of mechanical pressure changes within the ultrasonic field on the microbubbles. In the context of the present invention, shear forces are associated with cavitating microbubbles within dental fluid that are distributed along the surfaces of the gums and teeth, as well as in interproximal and subgingival spaces. Microstreaming induced by the ultrasonic acoustic energies used in devices of the present invention produces shear stresses of between about 0.1 Pa and about 1000 Pa. Devices of the present invention preferably operate at acoustic operating parameters to produce shear stresses of between about 0.2 Pa and about 500 Pa and, in some embodiments, produce shear stresses of from about 0.3 Pa to about 150 Pa. In yet other embodiments, shear stresses produced by devices of the present invention are from about 1 Pa to about 30 Pa. These shear stresses remove plaque and/or stains on the surfaces of teeth and other structures in the oral cavity and disrupt biofilm.

Oral hygiene devices of the present invention are capable of generating fluid flows within a fluid operating environment at a range of from about 0.5 cm/sec to about 50 cm/sec at a distance of between about 1 mm and 10 mm beyond the toothbrush bristle tips and/or acoustic waveguide. More typically, toothbrushes of the present invention are capable of generating fluid flows within a fluid operating environment at a range of about 1 cm/sec to about 30 cm/sec at a distance of between about 1 mm and 10 mm beyond the toothbrush bristle tips and/or acoustic waveguide. Oral hygiene devices are preferably capable of generating fluid flows of between 2 and 10 cm/sec at a distance of between about 1 mm and 10 mm beyond the toothbrush bristle tips and/or acoustic waveguide.

An Exemplary Device

FIG. 1 schematically illustrates an exemplary oral hygiene device of the present invention, a toothbrush, comprising an ultrasound transducer, an acoustic waveguide, and a motor for generating oscillations at sonic frequencies in a toothbrush. Toothbrush 10 comprises a handle 15 constructed from a rigid or semirigid material, which typically houses at least one rechargeable battery 12 that is preferably adapted to be induction charged using a charging device powered by an external power source (not shown); electrical circuitry, including an ultrasonic module drive circuit 14; a motor 16 for generating oscillation at sonic frequencies, preferably a DC motor for driving toothbrush head 20 at sonic frequencies; and controller 18 that provides timing, motor control and various other control functions. Suitable motors, ultrasonic drive circuits, rechargeable batteries, and controllers are well known in the art and may be used in devices of the present invention. Ultrasonic module drive circuit 14 is coupled to an ultrasound transducer for producing acoustic energy at ultrasonic frequencies at the brush head and motor 16 is coupled to the brush head to produce acoustic energy at sonic frequencies at the brush head.

Toothbrush head 20 is mounted on handle 15 and includes a stem portion 21 and brush head portion 23. Stem portion 21 may provide a channel or other means for facilitating transmission of ultrasound drive instructions, power and sonic oscillations to the brush head portion. Brush head portion 23 comprises an ultrasound transducer 22 and an acoustic waveguide 24 in operable proximity and acoustically coupled to the ultrasound transducer. In the toothbrush embodiment illustrated schematically in FIG. 1, an optional ultrasound reflecting element 28 is shown behind, and extending around each side of, the ultrasound transducer 22 that reflects the ultrasound through the acoustic waveguide 24 and into the dental fluid. The toothbrush head 20 may be either detachably or fixedly attached to the handle 15 and, in preferred embodiments, is detachably mountable to handle 15. The brush head portion may then be provided as a separate, replaceable component.

In general, toothbrush head 20 includes a plurality of bristle tufts 26 disposed adjacent to and generally surrounding acoustic waveguide 24. The toothbrush head 20 may optionally include an impedance matching layer 29 mounted between ultrasound transducer 22 and acoustic waveguide 24. Impedance matching layer 29 may improve the efficiency of the device, as discussed below. All of these components are described in greater detail below with reference to specific embodiments.

Alternating current supplied by the ultrasonic module drive circuit 14 (from a rechargeable power source) drives ultrasonic transducer 22 such that the transducer 22 expands and contracts primarily along one axis at or near resonance with the frequency supplied by the ultrasonic module drive circuit 14, thereby converting electrical energy into acoustic energy at ultrasound frequencies. The resulting ultrasonic acoustic waves are conducted into, propagated through, and radiated out of acoustic waveguide 24. The transmitted ultrasonic acoustic energy acts on microbubbles within fluid in the oral cavity (typically a mix of saliva, water and dentifrice) to induce cavitation, thereby loosening plaque deposited on the teeth and in interproximal regions.

The device of FIG. 1 illustrates an exemplary oral hygiene device of the present invention in the form of a power toothbrush. Additional and preferred embodiments including various ultrasound and/or sonic operating parameters, device components, control features, and the like, are described in greater detail below. It will be appreciated that while certain combinations of operating parameters and features may be preferred for use in certain applications and in particular environments, the device components, operating parameters, control features, and the like, may be combined in many different ways in oral hygiene devices of the present invention.

It will also be appreciated that these features may be used in various types of oral hygiene devices and, indeed, in other types of devices, and the inventions described herein are not limited to oral hygiene and toothbrush embodiments. In alternative embodiments, for example, devices may have a support structure, such as a handle and/or a device head, having at least one implement projecting from the support structure. The projecting implement may be an acoustic waveguide, a bristle tuft, a prong, a holder for a detachable implement or material, or the like. In preferred embodiments, the projecting implement is acoustically coupled to an ultrasound transducer. The device may additionally incorporate one or more bristle tuft(s) and one or more motor(s) for producing oscillation of the device head and/or projecting implement at sonic frequencies.

Ultrasound Operating Parameters

Ultrasound operating parameters for oral hygiene devices of the present invention incorporating an ultrasound transducer assembly include: the ultrasound frequency; the pulse repetition frequency (PRF); the number of cycles per burst; the duty cycle; the power of the ultrasound transducer; the peak negative acoustic pressure generated by the ultrasound transducer; and the environment in which the device is operated.

Ultrasound transducer assemblies incorporated in oral hygiene devices of the present invention generally operate at a carrier frequency (i.e., the frequency of the individual ultrasound waves) greater than about 20 kHz; typically between about 30 kHz and about 3 MHz; typically less than 1.5 MHz; and more typically less than 1.0 MHz, which is lower than the operating frequency of many ultrasonic toothbrushes. In many embodiments, the preferred ultrasound carrier frequency is between about 100 kHz and about 750 kHz; in some embodiments between about 100 kHz and about 600 kHz; in still other embodiments between about 150 kHz and about 500 kHz; and, in yet other embodiments, between about 250 kHz and about 500 kHz. It will be understood that the optimal range of the carrier frequency for different applications may vary depending upon the available bubble population, the size and power of the ultrasound transducer employed, and the conditions prevalent in the operating environment—e.g., the composition of fluids, and the like.

Ultrasound may be applied continuously or may be pulsed in a regular or irregular pattern of on/off periods. For many applications, ultrasound is pulsed to produce a predetermined number of waves within a packet or burst (cycles/burst) at a predetermined pulse repetition frequency (PRF). The duty cycle (i.e., the percentage of time that the ultrasound is activated) is related to the PRF and the number of bursts per cycle. A 100% duty cycle represents continuous ultrasound application. Ultrasound duty cycles of less than 100% may be achieved in many ways. For example, ultrasound may be "packaged" into bursts wherein the number of cycles per pulse and the pulse (burst) repetition frequency is varied to achieve a desired duty cycle. A 10% duty cycle of a 100,000 Hz (100,000 cycles per second) ultrasound signal yields 10,000 cycles. These 10,000 cycles may be delivered in a single burst of 0.1 second duration, followed by a 0.9 second off state (burst length=10,000, pulse repetition frequency=1 Hz). Alternately, 10,000 cycles may be delivered in 10 bursts of 1,000 cycles each (burst length=1,000, pulse repetition frequency=10 Hz) for a total ultrasound on time of 0.1 s (i.e. 10*0.01 sec. pulses) and 0.9 sec. (i.e. 10*0.09 sec pulse) of off time.

In general, dental plaque and biofilm removal increases with increasing duty cycle. Practical levels of ultrasound duty cycle may, however, be limited by factors such as transducer operating characteristics (power consumption, internal heating, etc.), safety to tissue (thermal index, tissue heating, etc.), user feel and preference, and the like. For oral hygiene applications where the device is operating in a typical dental slurry, ultrasound duty cycles of from about 1 to 30% are typical, with duty cycles of about 4 to 20% being most common, and duty cycles of from about 4 to 15% being preferred. Higher duty cycles may be preferred for use in particular applications.

The desired ultrasound PRF may depend upon the ultrasound frequency, the number of cycles per burst, and the environment in which the toothbrush is operating, including the composition and physical properties of the fluid medium into which the ultrasonic energy is being transmitted. Typically, though not exclusively, in oral hygiene devices of the present invention, the PRF ranges from about 0.5 Hz and about 10,000 Hz; more typically between about 0.5 Hz and about 2,500 Hz, and still more typically between about 1 Hz and about 500 Hz. In toothpaste, for example, a preferred PRF at a 10% duty cycle is generally less than about 20 Hz and may be less than about 10 Hz. In an aqueous environment, though, a higher PRF may be used, typically over 40 Hz and often in the range of between 40 to 200 Hz. In some embodiments of oral hygiene devices of the present invention that use ultrasound frequencies in combination with sonic frequencies, the PRF is a small multiple (generally two or greater, more typically four or greater) of the sonic frequency (i.e., the frequency of movement of the bristles and/or acoustic waveguide driven by a sonic component of a toothbrush of the present invention).

The number of individual ultrasound waves within a packet or burst of ultrasound (cycles per burst) is another ultrasound operating variable and, in oral hygiene devices of the present invention, is typically between about 10 and about 10,000 cycles/burst and, for many embodiments, between about 500 and 10,000 cycles/burst. The desired number of cycles per burst may depend, for example, upon the ultrasound frequency, the PRF, and the environment in which the toothbrush is operating. For promoting acoustic microstreaming in the context of devices of the present invention, relatively long bursts and relatively low PRF are suitable.

Generally, less frequent pulses of a greater number of cycles is preferred to more frequent pulses of a lesser number of cycles. Operating in the environment of a dentifrice slurry generally requires more cycles per pulse than a 100% water medium requires to achieve comparable biofilm removal. In a dental slurry, 100 to 10,000 cycles per pulse is common, with 500 to 5000 pulses being even more typical. The pulse repetition frequency can be calculated based upon the desired duty cycle. For example, for a 250,000 kHz ultrasound signal, a 10% duty cycle, and an ultrasound package of 1000 cycles per burst, the pulse repetition frequency is 25 Hz (i.e. 250,000 kHz×0.10÷1000 cycles/burst=25 Hz).

The ultrasound operating parameters preferred to provide optimal cleaning and user experience vary depending, for example, on the composition and character of the fluid environment in which the device is operated. Toothbrushes are operated in the oral cavity where fluids such as saliva and water are typically mixed with toothpaste or another cleaning agent to form a slurry. A typical dental slurry is more viscous than water and may be more or less acoustically transmissive than a water/saliva mix. For toothbrush and other oral hygiene devices operating in a typical toothpaste dental slurry environment, the combinations of operating parameters described in the table below are suitable.

| Ultrasound Frequency Range | Duty Cycle | Cycles/Burst | PRF (Hz) |
|---|---|---|---|
| 100-750 kHz | 5% | 500-10,000 | 0.5-75 |
| 100-750 kHz | 10% | 500-10,000 | 1.0-150 |
| 100-750 kHz | 15% | 500-10,000 | 1.5-225 |
| 250-500 kHz | 5% | 500-10,000 | 1.3-50 |
| 250-500 kHz | 10% | 500-10,000 | 2.5-100 |
| 250-500 kHz | 15% | 500-10,000 | 3.8-150 |
| 300 kHz | 5% | 500-10,000 | 1.5-30 |
| 300 kHz | 10% | 500-10,000 | 3.0-60 |
| 300 kHz | 15% | 500-10,000 | 4.5-90 |

Other types of devices may be used in a substantially aqueous (water) environment, and the operating parameters may be adjusted accordingly. For oral hygiene devices operating in a substantially aqueous environment, the combinations of operating parameters described in the table below are suitable.

| Ultrasound Frequency Range | Duty Cycle | Cycles/Burst | PRF (Hz) |
|---|---|---|---|
| 100-750 kHz | 5% | 50-1,000 | 5-750 |
| 100-750 kHz | 10% | 50-1,000 | 10-1500 |
| 100-750 kHz | 15% | 50-1,000 | 15-2250 |
| 250-500 kHz | 5% | 50-1,000 | 12.5-500 |
| 250-500 kHz | 10% | 50-1,000 | 25-1000 |
| 250-500 kHz | 15% | 50-1,000 | 37.5-1500 |
| 300 kHz | 5% | 50-1,000 | 15-300 |
| 300 kHz | 10% | 50-1,000 | 30-600 |
| 300 kHz | 15% | 50-1,000 | 45-900 |

In yet another embodiment, oral hygiene devices of the present invention having an ultrasound transducer, such as a toothbrush, operate at an ultrasound frequency of greater than about 250 and less than about 350 kHz, at a duty cycle of about 10% with about 5,000 cycles per burst at a pulse repetition frequency of about 6 Hz. In yet another embodiment, an oral hygiene device of the present invention having an ultrasound transducer, such as a toothbrush, operates at an ultrasound frequency of greater than about 250 and less than about 350 kHz, at a duty cycle of about 10% with about 500 cycles per burst at a pulse repetition frequency of about 60 Hz.

Various combinations of ultrasound operating parameters may also be used to promote acoustic streaming. For oral hygiene applications in which it's desired to promote acoustic streaming, the following ranges of ultrasound parameters are generally employed: (1) the carrier frequency is typically greater than about 20 kHz; more typically, between about 500 kHz and about 5,000 kHz or more, to enhance acoustic absorption; (2) the pulse repetition frequency (PRF) is typically, though not exclusively, between about 1 Hz and about 10,000 Hz; more typically between about 10 Hz and about 10,000 Hz; still more typically between about 100 Hz and about 10,000 Hz; and yet more typically, greater than about 1000 Hz and less than about 10,000 Hz; and (3) the number of individual ultrasound waves within a packet or burst of ultrasound is typically between about 1 and 5,000; more typically between about 5 and about 100 waves. For oral hygiene applications in which it's desired to promote acoustic streaming, longer duty cycles are typical, such as, for example, at least about 10%; more typically at least about 25%; still more typically at least about 50% or at least about 75% and, in some embodiments, up to 100%. Longer bursts, e.g., greater than about 100 waves at a frequency of about 1 MHz, with a PRF of at least 1000 Hz, are exemplified herein. It will be apparent that different burst lengths, frequencies, and PRF values may be suitably employed in oral hygiene devices of the present invention.

The magnitude of the acoustic output of the ultrasound transducer assembly and the acoustic waveguide affects the disruption of dental plaque biofilm, as does the composition of the fluid media. In general, higher acoustic output yields greater bubble activation and improved cleaning, plaque removal and biofilm disruption. One measure of acoustic output from an ultrasound transducer is the peak negative acoustic pressure measured during an operating cycle. Suitable operating peak negative acoustic pressure parameters in oral hygiene devices of the present invention are generally in the range of from about 0.01 to 10 MPa; more typically in the range of from 0.1 to 5 MPa; for many embodiments in the range of from 0.1 to 1 MPa; for many embodiments in the range of from 0.25 to 0.6 MPa; and in yet other embodiments in the range of from 0.3 to 0.5 MPa.

"Mechanical index" refers to a measure of the onset of cavitation of a preexisting bubble subjected to one cycle of applied acoustic pressure. The mechanical index is defined as the square root of the ratio of peak negative pressure (in MPa) to the ultrasound frequency (in MHz) and provides a means to quantify the acoustic output of an ultrasonic transducer. To produce a specific cleaning effect, a device operating in a fluid medium that is substantially aqueous (e.g., 100% water) requires a lower mechanical index than a device operating in a more viscous fluid medium, such as a saliva/water/dentifrice fluid. In a typical dental slurry fluid environment, a mechanical index of at least about 0.25 is generally required to achieve plaque removal. In a relatively low viscosity aqueous (water) environment, a mechanical index of at least 0.1 is generally required to achieve plaque removal. If the mechanical index is reduced below these threshold levels, the removal of significant dental plaque biofilm is generally not achieved even if the ultrasound duty cycle is increased. Conversely, once the mechanical index exceeds the threshold level and is sufficient to produce a significant effect, the ultrasound duty cycle may be reduced without significant loss of plaque removal efficiency. Thus, for example, at a 10% duty cycle reducing the mechanical index by 50% (e.g., from 1.0 to 0.5) has a substantial effect on biofilm removal. Holding mechanical index at 1.0 while reducing duty cycle by 50% (e.g., from 10% to 5%), however, yields a substantially smaller effect on biofilm removal.

The mechanical indices delivered by devices of the present invention are generally in the range of about 0.001 to about 1000. More typically, mechanical indices are in the range of about 0.01 to about 20, still more typically in the range of about 0.02 to about 10, and even more typically in the range of about 0.1 to about 5, or between about 0.1 and about 1.9. Devices intended for operation in substantially aqueous environments preferably exhibit a mechanical index of greater than 0.1. In devices of the present invention intended for operation using a dentifrice or another relatively viscous composition in the oral cavity, the mechanical index is preferably greater than about 0.25 and less than 1.9 and, in other embodiments, the mechanical index is greater than about 0.25 and less than 1.5. Devices of the present invention, according to some embodiments, operate with a mechanical index of between about 0.5 and 1.5 and in yet other embodiments, between about 0.8 and 1.4.

Sonic Operating Parameters

Within certain embodiments, oral hygiene devices of the present invention incorporate a drive motor that generates oscillation at sonic frequencies in combination with an acoustic waveguide and/or an ultrasound transducer. A motor assembly that, when the device is activated, generates oscillations at sonic frequencies is typically mounted in a device handle and the oscillations are transmitted to the device head, thereby producing oscillation of the acoustic waveguide and/or bristle tufts. The motor may alternatively be mounted in a portion of the device head.

The acoustic waveform of sonic oscillations, as generated in devices of the present invention, is generally sinusoidal, but other waveforms may be used—additionally or alternatively. Sonic oscillations may be driven in non-sinusoidal waveforms, for example trapezoidal, triangular, square, purely rotational, and other waveforms. Additionally, the frequency and/or amplitude may be modulated. The frequency of sonic oscillation influences the effectiveness of cleaning produced by both the sonic and ultrasonic components, and may additionally influence user comfort and the user's perception of cleaning effectiveness.

In a device incorporating one or more bristle tufts, generation of oscillations at sonic frequencies at the brush head produces bristle tip motion. Bristle tip motion may be characterized by bristle tip velocity, amplitude, frequency, acceleration, and other metrics. Devices of the present invention employing a motor generating oscillations at sonic frequencies preferably operate to produce bristle tip frequencies of greater than 20 Hz and less than 20,000 Hz. High bristle tip frequencies are irritating to many users and may create an undesirable tickling sensation in the oral cavity. For this reason, bristle tip frequencies of less than about 2,000 Hz are preferred. A desired sonic operating frequency may be a note on the musical scale, most typically those have a frequency greater than about 54 Hz and less than about 1662 Hz. According to some embodiments, operating parameters producing bristle tip frequencies of less than about 1500 Hz are preferred; bristle tip frequencies of less than about 1000 Hz are preferred for many applications; bristle tip frequencies of less than about 500 Hz are preferred for yet other embodiments. In still other embodiments, bristle tip frequencies of greater than about 20 and less than about 500 Hz are preferred; in yet other embodiments, between 100 and 300 Hz.

To maintain a generally constant bristle tip velocity as the frequency increases, the bristle tip amplitude decreases. Similarly, to maintain a substantially constant bristle tip velocity as the amplitude increases, the frequency decreases. Both frequency and amplitude of bristle tip movement may affect cleaning and user comfort. Oral hygiene devices of the present invention, intended for use in the environment of a common dentifrice slurry and employing sinusoidal sonic motion, generally operate to produce a desired peak bristle tip velocity during an operating cycle, of from 0 to 10 m/s, more typically from 0.2 to 5 m/s, more typically from 0.4 to 1.5 m/s and generally less than 1.5 m/s. For many embodiments, the bristle tip velocity during operation is less than about 1.0 m/s, often less than 0.8 m/s, and in some embodiments between about 0.4 and 0.8 m/s. These bristle tip velocities are generally lower than the bristle tip velocities produced by many power toothbrushes that operate by oscillating bristle tufts at sonic frequencies. Bristle tip velocity measurements are taken with the bristles dry, in air, without an applied load to the bristle tips. Actual bristle tip velocity is generally reduced during operation as a result of loading associated with frictional contact of the bristles against teeth and drag associated with moving bristles through a fluid environment.

The bristle tip amplitude produced by sonic oscillation also influences the cleaning effectiveness provided by both sonic and ultrasonic components. The peak amplitude of bristle tip motion during an operating cycle or subcycle may range from about 0.01 to 10 mm. A preferred range of peak bristle tip amplitude (as wetted and typically loaded in the oral cavity) is in the range of 0.1 to 6 mm, and is generally less than 4.0 mm. According to further embodiments, the peak bristle tip amplitude is less than 3.0 mm and may be in the range of from 0.2 to 3.0 mm or from 0.4 to 2.2 mm. This is lower than the peak bristle tip amplitudes of many power toothbrushes that operate by moving bristles at sonic frequencies. Bristle tip amplitude measurements are taken with the bristles dry, in air, without an applied load to the bristle tips.

The Acoustic Waveguide

As indicated above, oral hygiene devices of the present invention incorporate an acoustic waveguide projecting from the device head support structure in combination with an ultrasound transducer and/or a motor oscillating at sonic frequencies. The acoustic waveguide provides a conduit for the transmission of ultrasound waves from the ultrasound transducer, where they are generated, through an (optional) impedance matching layer, to fluid in the oral cavity and is substantially more efficient and effective than the bristle tufts in transmitting the ultrasound acoustic energy to fluids in the oral cavity. Thus, devices of the present invention direct ultrasound through a waveguide structure and substantially isolate it from the bristle tufts. The dental fluid into which the acoustic waveguide is immersed during use of the device in the oral cavity is typically a saliva and toothpaste emulsion that is acoustically absorptive and, in the absence of an acoustic waveguide, the fluid would attenuate significant amounts of the ultrasound before the wave front reached the tooth and gum surfaces. Impedance mismatches are also a significant barrier to sound transmission from an ultrasound transducer to the tooth and gum surfaces. The acoustic waveguide serves as a bridge across the acoustic mismatch by transmitting acoustic energy at ultrasound frequencies into the saliva and toothpaste emulsion near the tooth surface.

Typically, as shown in FIG. 1, the acoustic waveguide is positioned at the base of a brush head portion of the device in proximity to one or more bristle tufts. According to preferred embodiments, the acoustic waveguide is in operable proximity and acoustically coupled to an ultrasound transducer and transmits acoustic energy at ultrasound frequencies to the fluids in the oral cavity. The acoustic waveguide, as described previously, may additionally be oscillated at sonic frequencies.

A variety of acoustic waveguide designs are contemplated for use in devices of the present invention. Two parameters substantially affect the transmission of ultrasonic waves through an acoustic waveguide: (1) the material(s) from which the waveguide is fabricated; and (2) the geometry of the waveguide. Each of these parameters is described in further detail herein. In addition, the acoustic waveguide must have a pleasant mouth feel and must present a surface that is soft enough to be appealing when it is oscillated at sonic frequencies and contacts the oral cavity and teeth. Acoustic waveguides having an appealing texture and softness are designed to efficiently receive, conduct, coherently focus, incoherently compress, and transmit out the acoustic energy at ultrasound frequencies. Acoustic waveguides may also be designed to channel acoustic energy along the waveguide, and transmit or "leak" acoustic energy into the surrounding medium before it has propagated to the end of the waveguide. One way to promote this acoustic leakage is to fabricate the waveguide from a material having a sound speed substantially lower than that of the surrounding fluid and/or to provide a waveguide having tapered side walls.

The acoustic waveguide, in general, has a solid, block-like structure with at least one dimension that is substantially larger than that of an individual bristle tuft. The dimensions of the acoustic waveguide are determined by design parameters such as the ultrasound transducer face area, mounting considerations, the feel of the waveguide in the user's mouth, and the arrangement of bristle tufts. The acoustic waveguide is in operable proximity and acoustically coupled to the ultrasonic transducer and adjacent to and flanking, on one or more sides, bristle tufts. The size and configuration of the base of the acoustic waveguide, in the embodiment illustrated in FIG. 1, generally matches the size and configuration of the exposed surface of the ultrasound transducer and/or an associated impedance matching layer and is mounted contacting an exposed surface of the ultrasound transducer and/or an associated matching layer. The body of the acoustic waveguide may form a generally rectangular solid or may have one or more curved profiles, as shown in FIG. 1.

In some embodiments, at least one of the waveguide walls is tapered so that the tip, or distal face, of the acoustic waveguide distal from the ultrasonic transducer has a smaller cross-sectional area than that of the base of the acoustic waveguide in proximity to the ultrasound transducer. In general, the acoustic waveguide has a length, often oriented generally along the longitudinal axis of the brush head, that is greater than the diameter of a bristle tuft and, more preferably, has a length that is greater than the (side-to-side) combined diameters of at least two bristle tufts. In another embodiment, the length of the acoustic waveguide is greater than the (side-to-side) combined diameters of at least five bristle tufts. In another dimension, the width of the acoustic waveguide, often oriented generally transverse to the longitudinal axis of the brush head, at its base, is generally greater than the diameter of a bristle tuft and, in some embodiments, is generally greater than the (side-to-side) combined diameters of at least two bristle tufts. The structure and composition of many alternative acoustic waveguides that are suitable for use in devices of the present invention are described in detail in U.S. Patent Publication 2005/0091770 A1, which is incorporated herein by reference in its entirety.

In general, acoustic waveguides are constructed from a material that is somewhat "soft" and "rubbery," such as a silicone rubber, or other types of biocompatible materials, such as other types of rubbers, thermoplastic elastomers, and closed or open cell foams having good ultrasound transmission properties and a pleasing feel and surface texture. The hardness of the material is generally less than about 80 Shore A, and more often is from approximately 10 to 65 Shore A. A hardness of approximately 40 Shore A or less may be employed in order to achieve improved oral comfort. In some embodiments, acoustic waveguides may have a composite structure in which a relatively harder material is provided in proximity to the ultrasound transducer and a relatively softer material is provided in proximity to the distal face of the waveguide. The hardness of the waveguide in proximity to the ultrasound transducer may be greater than about 40 Shore A, for example, while the hardness of the waveguide in proximity to the distal face may be less than about 40 Shore A, for example. The waveguide material properties may be isotropic or anisotropic.

In one embodiment, the height of the acoustic waveguide exposed when the waveguide is mounted in the brush head is less than the exposed height of at least one bristle tuft and, in another embodiment, the height of the acoustic waveguide exposed when the waveguide is mounted in the brush head is less than the exposed height of each of the bristle tufts mounted in the brush head. In another embodiment, the height of the exposed acoustic waveguide portion is greater than at least one bristle tuft provided in the brush head. In general, the exposed height of the acoustic waveguide is greater than about 30% and less than about 90% of the exposed height of the bristle tufts. In yet another embodiment, the exposed height of the acoustic waveguide is greater than about 40% and less than about 80% of the exposed height of the bristle tufts.

The distal face of the waveguide may be curved or flat. In some embodiments, the cross-sectional area of the waveguide at its distal face is at least five times greater than that of a bristle tuft; in another embodiment, the cross-sectional area of the waveguide at its distal face is at least ten times greater than that of a bristle tuft; and in another embodiment, the cross-sectional area of the waveguide at its distal face is at least twenty times greater than that of a bristle tuft. The surface of the acoustic waveguide is substantially smooth in many embodiments; in alternative embodiments it may be textured in a regular or irregular pattern.

Materials having suitable ultrasound transmission properties, desired hardness and feel, and the like, are well known in the art. Silicone rubber and other types of rubbers, silicone materials such as castable/moldable RTV, liquid injection-molded (LIM) silicone, thermoplastic elastomers, thermal plastic elastomer (TPE) injection-molded processes, and closed or open cell foams may all be used. Polymers have an advantage over other waveguide materials, owing to their relatively low shear wave velocity. However, because of their viscoelasticity, cross-linking of polymeric materials may be necessary to avoid excessive acoustic loss and provide equilibrium elastic stress, thus providing a more stable waveguide composition.

The acoustic waveguide may optionally incorporate an acoustic impedance matching device, such as a matching layer of graphite, mineral, or metal-filled epoxy. Various dielectric materials, such as silicon dioxide ($SiO_2$), silicon nitride ($Si_3N_4$), and many other polymers may also be used as or incorporated in an acoustic impedance matching device. The matching layer may be embedded or incorporated in the waveguide and positioned to contact an exposed face of the ultrasound transducer. In another embodiment, the functions of a matching layer and waveguide may be combined by fabricating a stratified waveguide component with varying acoustical impedance in the direction of wave propagation. Thus, within certain embodiments, acoustic waveguides of the present invention may comprise two or more layers comprising different, acoustically transmissive materials. For example, acoustic waveguides comprising three, four, and/or five acoustically transmissive layers are contemplated for certain applications. Multiple layers may be provided in a symmetrical laminar structure; regular or irregular areas composed of different materials may also be provided. Acoustic waveguides may further comprise one or more inserted or embedded elements for shaping the acoustic properties, promoting acoustic propagation and optimizing sonic properties. A waveguide assembly may include, for example, a graphite core portion or similar component that may be inserted into an injection mold, and an elastomeric outer portion molded around it using an insert molding process. Alternatively, a multishot molding approach may be used to create a gradient of materials with different acoustic and/or elastomeric properties.

In preferred embodiments, acoustic waveguides of the present invention are substantially free from unfilled or gas-filled voids. To the extent that multiple materials or elements are used to form a waveguide, those materials and elements generally contact each other closely without allowing the formation of air gaps between surfaces. In some embodiments, however, it may be desirable to form one or more voids in the acoustic waveguide and substantially fill the voids with a material that has desirable acoustic transmission properties at the ultrasound operating parameters described herein.

The acoustic waveguide may also be fabricated, or mounted in the device head structure, to provide direct contact removal of plaque. In such an embodiment, the distal face of the waveguide may project beyond the ends of one or more bristle tuft(s). Auxiliary elements may be incorporated on the surface of the waveguide structure such as embedded bristle filaments, squeegee-type shapes, molded or shaped protrusions similar to bristles, and the like, and such auxiliary elements may be provided in an ordered or random pattern. These features may, optionally, be exploited to ensure that a specified separation distance is maintained between the tooth surface and the bulk surface of the acoustic waveguide. This optional feature may be incorporated in those applications wherein it is desired to minimize direct transmission of ultrasound into the tooth structure and/or if bubble activation occurs at a distance from the end of the acoustic waveguide and a spacing device is needed to maintain this distance.

According to yet further embodiments, the acoustic waveguide may be provided with a coating, or an outer layer, that is continuous or discontinuous, of a uniform or variable thickness, and that comprises a material providing additional functionality. In one embodiment, for example, the acoustic waveguide may be fabricated from a material that is coated or impregnated with an antimicrobial or antifungal agent that is biocompatible, such as a metal ion such as silver or another antimicrobial agent. In another embodiment, the acoustic waveguide may be coated or overlaid with a substance that wears away with use to indicate that the acoustic waveguide and toothbrush head has reached the end of its useful life. Suitable indicators may include, for example, substances that produce a change in a property, such as color, flavor, texture, and/or odor over periods of extended use. In yet another embodiment, the waveguide may incorporate a thermally activated color changing agent, such as a dye, that senses heat generated by a functional piezoelectric transducer. This feature may be used, for example, in combination with a charging function that allows the ultrasonic generator to add heat to the acoustic waveguide and thereby change its color during the time that the batteries are also being charged.

The waveguide may be positioned generally aligned with the longitudinal axis of the toothbrush head, as shown in FIG. 1. In this configuration, the waveguide may be structured to approximately match the contour of tooth surfaces throughout the mouth. The efficacy of the cleaning operation may depend less on user brushing technique/style with the waveguide in this longitudinal orientation, which allows the user to brush as he/she would without concern about waveguide location. Alternatively, the longitudinal axis of the waveguide may be aligned generally transverse to longitudinal axis of the toothbrush head. In this orientation, the waveguide may be designed to drop into the interproximal space and provide tactile feedback to the user such that the user may index movement from one interproximal space to the next, thus providing cleaning induced by the ultrasound interproximally—where it is needed most beyond the bristles. Alternatively, the waveguide may be positioned at the distal end of the brush head without bristle tufts being located more distally, such that it can be effectively used either on the facial or lingual surfaces, as well as on the posterior surfaces of the molar teeth.

The waveguide, in any of these orientations may act as a standoff to prevent the user from using too much force when applying the bristles against the teeth, thereby reducing the incidence of gingival damage from excessive force during brushing. It may also act as a scrubbing agent, thus cleansing the tooth surface, and as such may contain a surface texture to enhance the scrubbing action. It may also act as a gum massaging agent, thus stimulating the gums (as often recommended by the dental profession) to reduce swelling and to help contour the tissue. It may additionally function to stimulate saliva flow, which is particularly of interest to individuals with xerostomia.

The structure and composition of the waveguide may be designed to increase the acoustic intensity delivered by compressing the acoustic field, and/or to coherently focus energy into the surrounding media beyond the tip of the waveguide. This may be accomplished, for example, by shaping the end of the acoustic waveguide to produce an acoustic lens effect that focuses the waves from the waveguide into a higher intensity field beyond the waveguide. This focusing effect may be achieved with one or multiple waveguide materials combined together and shaped to create a focused field. For instance, a low attenuation, higher sound speed material may be used at the end of the waveguide to continue propagating and focusing the wave front before the wave front emerges into the higher attenuation fluid environment of the oral cavity. As with the acoustic field compression described above, the increased acoustic intensity achieved with the focusing effect improves the device efficiency.

The Ultrasound Transducer

As described above, certain embodiments of the present invention provide an oral hygiene device employing an ultrasound transducer to generate ultrasonic energy in combination with an acoustic waveguide to efficiently propagate ultrasonic energy into the dental fluid. Microbubbles, present in the dental fluid as a result of the movement of bristle tufts and/or formed by sonic oscillation of bristle tufts and/or an acoustic waveguide, are stimulated, through ultrasound energy-induced cavitation, to produce "scrubbing bubbles" that are effective in loosening and removing plaque from exposed tooth surfaces and at interproximal regions at a distance from the toothbrush head. The ultrasonic transducer disclosed herein causes these microbubbles to pulsate, thereby generating local fluid motion around the individual bubbles and producing microstreaming that, in combination with the ultrasonic cavitation effects, achieves shear stresses that are sufficient to disrupt plaque.

The ultrasound transducer is generally mounted in a device head or brush head portion of an oral hygiene device of the present invention in proximity to the location of ultrasound emission to fluids in the oral cavity. An ultrasound transducer may, alternatively, be placed within the toothbrush handle and communicate with the device head to produce ultrasound emissions at or near the device head. By utilizing an extended coupler fabricated out of a low loss material such as titanium and/or steel protruding into a device head portion, acoustic energy may be coupled into a waveguide on the toothbrush head as described above. Acoustic coupling between the handle and an acoustic waveguide in the toothbrush head may, for example, be achieved using a solid or liquid material that turns the acoustic energy 90-degrees with respect to the longitudinal axis of the handle and toothbrush plastic. Such a coupling mechanism preferably employs a functional interface that permits the brushing portion of the toothbrush to be removed and replaced.

Ultrasound transducers that may be suitably employed in the oral hygiene devices of the present invention are readily available. See, e.g., ultrasound transducers disclosed in U.S. Pat. Nos. 5,938,612 and 6,500,121, each of which is incorporated herein by reference in its entirety. Ultrasound transducers suitable for use in devices of the present invention generally operate either by the piezoelectric or magnetostrictive effect. Magnetostrictive transducers, for example, produce high intensity ultrasound energy in the 20-40 kHz range. Alternatively, ultrasound may be produced by applying the output of an electronic oscillator to a wafer of piezoelectric material, such as lead zirconate titanate (PdZrTi or PZT). Numerous piezoelectric PZT ceramic blends are known in the art and may be used to fabricate ultrasonic transducers suitable for use in devices of the present invention. Other piezoelectric materials, such as piezopolymers, single or multi-layer polyvinylidene fluoride (PVDF), or crystalline piezoelectric materials, such as lithium niobate ($LiNbO_3$), quartz, and barium titanites, may also be used.

In addition to piezoelectric materials, capacitive micromachined ultrasonic transducer (cMUT) materials or electrostatic polymer foams may also be used in ultrasound transducers of the present invention. Many of these materials can be used in a variety of oscillational modes, such as radial, longitudinal, shear, etc., to generate the acoustic waves. In addition, single-crystal piezoelectric materials may be used to reduce the lead content of the piezoelectric element(s). Materials such as $Pb(Mg_{1/3}Nb_{1/3})O_3$—$PbTiO_3$ (PMN-PT), $K_{1/2}Na_{1/2}NbO_3$—$LiTaO_3$—$LiSbO_3$ (KNN-LT-LS) and others may be used to reduce voltage/transmit level ratios by as much as an order of magnitude, as described in Lead-free piezoelectric ceramic in the $K_{1/2}Na_{1/2}NbO_3$ solid solution system, N. Marandian Hagh, E. Ashbahian, and A. Safari presented at the UIA symposium March 2006.

Ultrasound transducer assemblies used in devices of the present invention may comprise single piezoelectric elements that have a generally block-like form and generally rectangular configuration, as shown in FIG. 1. Such single element transducer assemblies may be provided in a variety of other configurations, such as cylindrical, elliptical, polygonal, annular, or the like and may have configurations that are symmetrical or asymmetrical. A single element ultrasound transducer may have a generally uniform cross-sectional configuration and dimension along its thickness, or it may taper or have another varied cross-sectional configuration.

Piezoelectric ultrasound transducer materials generally require a drive voltage that is proportional to the thickness of the piezoelectric element. A single piezoelectric element having a substantial thickness requires a high drive voltage. Thus, in alternative embodiments, devices of the present invention incorporate multi-layer ultrasound transducer elements, or multi-element transducers, to reduce the drive voltage required for a given acoustic output. Multiple piezoelectric element transducer assemblies are preferably constructed with the piezoelectric elements arranged mechanically in series and connected electrically in parallel. This arrangement reduces the drive voltage required for a given transducer output.

Figure 2A:
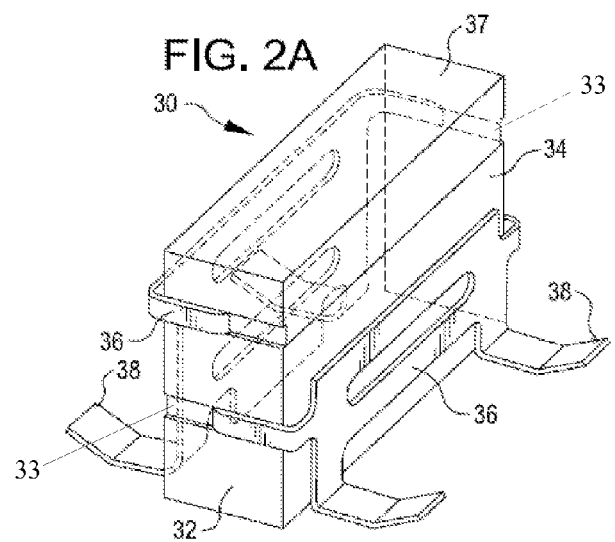
FIG. 2A is an enlarged schematic perspective view of an exemplary ultrasound transducer assembly and associated matching layer and electrical contacts suitable for use in devices of the present invention.
Figure 2B:
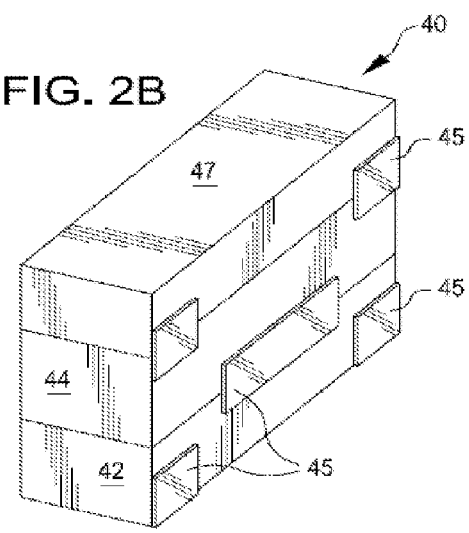
FIG. 2B is an enlarged schematic perspective view of another exemplary ultrasound transducer assembly and associated matching layer incorporating electrical contacts suitable for use in devices of the present invention.

FIGS. 2A and 2B illustrate exemplary ultrasound transducer assemblies suitable for use in oral hygiene devices of the present invention. In the embodiment illustrated in FIG. 2A, an ultrasound transducer assembly suitable for use in toothbrushes of the present invention comprises two or more piezoelectric elements arranged in a cooperating configuration, such as a stacked configuration, and bonded to one another. Ultrasound transducer assembly 30 has an overall generally rectangular or trapezoidal profile and comprises at least two piezoelectric elements 32 and 34 having electrically conductive material associated with one or more surfaces and one or more electrical contact(s) 36 contacting a conductive surface of each of the piezoelectric elements and in electrical contact with an ultrasonic module drive circuit located in the brush head or in the handle. Electrical contact(s) 36 in this embodiment are provided as an electrically conductive framework structure that tightly contacts the transducer assembly at contact points and additionally provides mechanical integrity to the transducer assembly structure. Contact points of an electrically conductive framework structure with one or more piezoelectric element(s) are preferably arranged at or near nodal points of the piezoelectric elements where the amplitude of movement of the element(s) is reduced. The conductive framework structure may be spring loaded to provide pressure connections and/or soldered, welded, or conductive epoxy to make a more robust electrical connection.

In the embodiment illustrated in FIG. 2A, the piezoelectric elements are notched or grooved along at least a portion of their perimeter, indicated at notched region(s) 33. Notched region(s) 33 are electrically conductive to provide contact points for electrical contact(s) 36 at or near the location where multiple piezoelectric elements are bonded to one another. Electrical contact(s) 36 include prong-like contact extensions 38 for providing electrical contact to electrodes in communication with the ultrasound drive circuit. In the embodiment illustrated in FIG. 2A, contact extensions 38 extend from the transducer assembly structure and may be flexible or spring-loaded to provide positive contact with electrodes. Ultrasound transducer assembly 30 may also incorporate an impedance matching element 37.

There are a variety of ways to make electrical connections between the piezoelectric elements and the electrodes in contact with the ultrasound drive circuitry. Electrically conductive surfaces may be provided, for example, using various techniques such as plating, sputtering or soldering conductive materials, or applying conductive epoxy or another conductive material. FIG. 2B illustrates an alternative embodiment of a multi-element ultrasound transducer assembly 40 suitable for use in oral hygiene devices of the present invention. In this assembly, piezoelectric elements 42 and 44 and impedance matching element 47 are bonded in a stacked arrangement with an electrically conductive coating or layer provided on at least a portion of the element surfaces. Electrically conductive "pads" 45 are provided on external surfaces of the transducer assembly for connection to electrodes communicating with the ultrasound drive circuitry. This type of electrical connection is commonly used, for example, in multi-layer PCBA interconnects. An exterior lead frame may also be employed for ease of construction of transducer module and ease of assembly of the module into the brush head.

In preferred embodiments, multiple piezoelectric elements are stacked in series mechanically, and connected electrically in parallel. Mechanical stacking of the elements in series provides that the displacements associated with the individual piezoelectric elements are additive. Electrically connecting the piezoelectric elements in parallel provides that the capacitances associated with the individual piezoelectric elements are also additive. This arrangement provides a greater range of electronics driving possibilities.

In addition to the transducer elements, one or more impedance matching element(s) may be provided in association with the ultrasound transducer assembly to improve the efficiency and/or bandwidth when transmitting acoustic energy from the generally high-impedance transducer elements into the lower impedance acoustic waveguide materials. Generally, a matching material is chosen having a thickness that supports a quarter wave of the desired frequency and having acoustic impedance properties intermediate those of the two impedances to be matched. Appropriate impedance matching elements may comprise materials such as epoxy and metal particulate composites, graphite, and a host of other candidate materials known by and readily available to the skilled artisan. The configuration and cross-sectional area of the impedance matching element generally matches that of the distal face of the ultrasound transducer and the impedance matching layer is generally in close contact with an exposed, distal face of the transducer.

Within alternative embodiments, ultrasound transducer assemblies used in devices of the present invention may employ a flextensional transducer that comprises an active piezoelectric drive element and a mechanical shell structure. Such a shell or "cymbal" structure is used as a mechanical transformer, which transforms the high impedance, small extensional motion of the piezoelectric drive element into a low impedance, large flexural motion of the shell. Suitable flextensional transducers are known in the art. Using a flextensional transducer may eliminate the need for a matching layer.

Still further embodiments of devices of the present invention employ a transducer assembly comprising a transducer array. In one embodiment, a piezocomposite transducer array comprises a plurality of posts. These posts may be fabricated, for example, by dicing a block of piezocomposite material into many smaller sub-elements or by injection molding an array of these elements to shape. Depending upon the precise application contemplated, the piezocomposite material and arrays fabricated from such materials may offer improved properties for ultrasound transduction compared to bulk transducers, due to reduced acoustic impedance and a high coupling factor. Many types of piezocomposite materials are known; exemplary materials are described in "*The role of piezocomposites in ultrasonic transducers*," Wallace Arden Smith, 1989 IEEE Ultrasonics Symposium. The sensitivity of a composite transducer is primarily in the normal direction, thus decoupling transverse mechanical oscillational modes and the interference they cause. The net result is greater acoustic output with lower drive voltage.

The Ultrasound Module

The ultrasound transducer assembly may be incorporated in an ultrasound module that additionally comprises a transducer supporting structure, an optional matching layer(s), and an acoustic waveguide. One exemplary ultrasound module 50 incorporating the transducer assembly shown in FIG. 2A is illustrated in FIG. 3. In this ultrasound module, transducer assembly 30 comprising piezoelectric elements 32 and 34 and impedance matching element 37, with electrical contact structure 36 with electrical leads 38 is mechanically mounted in a substantially rigid supporting structure 52 that provides mechanical support for the transducer assembly and also serves to direct ultrasonic wave propagation through the optional matching layer(s) 37 and acoustic waveguide structure 55. Good mechanical connection and acoustical properties may be accomplished, for example, by positioning the supporting structure coupling features 53, 54 to coincide with areas of minimal motion (nodal mounting) on the piezoelectric ceramic, matching layer, and waveguide. Acoustic waveguide 55 is then mounted or molded onto the transducer assembly and support structure to provide close contact between the internal surfaces of the waveguide and the external surfaces of the transducer assembly and support structure.

The acoustic waveguide may be mounted to and contacting an upper surface of the transducer assembly, as illustrated in FIG. 1 or, in alternative embodiments, acoustic waveguide 55 may be mounted to and contacting the upper surface of the transducer assembly and at least a portion, and preferably a substantial portion, of the side walls of the transducer assembly and support structure, as illustrated in FIG. 3. The waveguide structure 55 comprises a base structure 56 sized to (at least partially) cover ultrasound transducer assembly 30 and having a configuration generally matching that of the ultrasound transducer assembly. Base structure 56 is generally mounted and anchored in a toothbrush head with distal waveguide portion 58 projecting outwardly from the brush head structure. Waveguide structure 55 is preferably provided as a unitary structure having a generally block-like, three-dimensional configuration and having multiple faces. In the embodiment illustrated in FIG. 3, the cross-sectional area of base structure 56 is generally larger than the cross-sectional area of distal waveguide portion 58 and opposing side walls 57 and end walls 59 terminate distally in a distal waveguide face 60.

Distal waveguide face 60 may be curved in a generally convex configuration, as illustrated in FIG. 3. In alternative embodiments, distal waveguide face 60 may be generally flat, curved in a generally concave configuration, or curved in a more complex configuration. The intersections of one or more of the waveguide faces may be rounded or chamfered, as shown, or they may form angular corners. Any of the acoustic waveguide materials and structures described herein or in U.S. Patent Publication 2005/0091770A1 may be used in connection with ultrasound modules incorporated in devices of the present invention.

The acoustic waveguide module is generally mounted in the head of an oral hygiene device, such as a toothbrush head, so that the acoustic waveguide projects from the support structure of the device head. Additional waveguide supporting structures may also be provided as structural features of the transducer module or the brush head structure. A waveguide support flange may be provided extending from the brush head support base or bristle plate, for example, in proximity to the perimeter of the waveguide structure to provide a rigid structure supporting the base of the waveguide.

Regardless of the precise configuration of the individual elements that comprise the ultrasound module, the piezoelectric element, matching layer and/or the acoustic waveguide are generally designed to transmit, and optionally focus, the acoustic energy at a desired location relative to the emanating surface(s) or to disperse the acoustic energy in a specific pattern. The ultrasound energy may, for example, radiate directly from a generating source such as a piezoelectric ceramic element directly into the oral cavity fluid without an intervening matching layer or waveguide. Alternatively, an acoustic waveguide may be placed directly on the piezoelectric ceramic. In still further alternative embodiments, the entire ultrasonic module, including the acoustic waveguide, may be fabricated from a piezoelectric polymer.

The Device Head Assembly

The device head assembly is preferably detachable from the handle assembly and replaceable. A toothbrush head assembly comprises a substantially rigid housing structure adapted to receive and support an ultrasound module, one or more bristle tufts, and components for transmitting power to the ultrasound module and for coupling oscillatory motion to the acoustic waveguide and bristle tufts. Electrical power may be provided to the ultrasound transducer by hardwired electrical connections established by positive contact of complementary electrical contacts mounted in the handle and brush head upon attachment of the brush head to the handle. Alternatively, a transformer assembly may be implemented to provide coupling and power transfer between the device head assembly and the handle.

One embodiment of a toothbrush head assembly is illustrated in FIG. 4. The housing structure of toothbrush head assembly 80 comprises a base portion 82 for attachment to a mating attachment region on the handle, a smaller cross-section stem portion 84 and a brush head support structure 86 in which an ultrasound module 50 and/or toothbrush tufts are mounted. In this embodiment, power is provided to the ultrasound module by means of a transformer having a primary coil and core mounted in the handle (described below) and a secondary transformer core 87 and transformer coil (and associated bobbin) 88 mounted in the base portion 82 of head assembly 80. Operation of the transformer to deliver power to the toothbrush head without requiring hardwired connections is described below.

Electrical connection between the secondary coil 88 mounted in the toothbrush head assembly and the ultrasound transducer assembly in the ultrasound module 50 is accomplished by means of (one or more) conductive electrodes 89 that contact the transducer assembly contact(s) and contacts provided at the secondary coil. One or more conductive electrode(s) 89 may be provided as conductive metal strips retained in channel(s) in the brush head assembly and may be molded into the brush head structure. Alternatively, flexible electrical connections (e.g., jumper-type connections) may be used between the transducer assembly contacts and the coil contacts. In an alternative embodiment, the electrical contacts attach mechanically to the non-moving part of the brush head housing so that the contact provides a spring force to return the brush head to a center position or another desired position.

The bristle tufts are mounted on a support plate 90 in proximity to ultrasound module 50. The support plate may have a variety of configurations, including rectangular, generally circular, generally oval or elliptical. The support plate may also function as an acoustic matching layer. This plate can be ultrasonically welded to the brush neck to provide a seal around the ultrasound module or may be integrally formed with support structure 86. The brush neck assembly is attached to the housing with coil and core.

The device head, including the bristle filaments, the bristle filament and/or tuft spacing and orientation, the bristle and/or tuft trim, the waveguide configuration and placement, and the support structure of the device head are generally designed to promote holding, trapping, and otherwise encumbering fluid. The device head may also be designed to actively pass the ultrasound through the bristle filaments and/or tufts. This may be accomplished by mounting the ultrasound transducer assembly immediately below one or more individual tuft(s) and/or filament(s) and eliminating the coupling of the ultrasound through the toothbrush base plastic, as done in prior art toothbrushes.

Device heads of the present invention, and particularly toothbrush heads, typically incorporate assemblages of one or more bristle tufts, each tuft comprising a bundle of one or more bristle filaments. Many types of bristle filaments are available and may be used in device heads of the present invention. In general, bristle filaments, and tufts, may be characterized by the material of the filaments, the diameter, cross-sectional configuration and exposed length of each filament and tuft, the stiffness or flexibility of filaments and tufts, and the like. The filaments within each tuft may comprise the same material and have the same dimensional properties, or more than one bristle type, shape or size may be incorporated in a single bristle tuft. Likewise, multiple bristle tufts forming the assemblage may comprise the same dimensional and/or physical properties, or bristle tufts having different dimensional properties, lengths, stiffnesses, and the like, may be provided in various arrangements on the brush head. The tufts may comprise bristle filaments of a particular shape and/or size to facilitate both cleaning and user experience. Bristles of a particular shape may be positioned and oriented to complement the presence of a waveguide in the brush head. For example, stiffer bristles and bristle tufts (having a generally greater filament cross section and/or shorter bristle length) may be positioned to facilitate orientation of the waveguide at a particular position with respect to the teeth, and softer bristles (having a generally smaller filament cross-section and/or longer bristle length) may be positioned to facilitate waveguide penetration at interproximal spaces.

Nylon bristle filaments are suitable for use in devices of the present invention. In many embodiments, each bristle tuft comprises from about 25 to 40 filaments; in further embodiments, each bristle tuft comprises from about 28 to 30 filaments. The diameter of each filament strand is generally from about 0.005-0.009 inch and, in embodiments preferred for some applications, the diameter of each filament strand is from about 0.005-0.007 inch. Each tuft is approximately 0.03-0.12" in diameter; preferably about 0.05-0.08" in diameter. Other types of oral hygiene devices of the present invention may comprise more or fewer tufts and tufts having different properties.

Individual bristle filaments may be solid or, alternatively, the filaments may be hollow. Hollow bristle filaments may serve as sources of gas that becomes entrapped and forms bubbles within the dental fluid. Gas may be passively channeled through the bristles or actively pumped through the bristles. In one embodiment, the center diameter of hollow filaments may be designed to promote formation of bubbles having a diameter that is resonant with the frequency of the applied ultrasound, i.e. bubbles whose diameter is roughly in the range from 13 to 65 µm. Alternatively, hollow bristle filaments may be filled with an acoustically transmissive material that conducts ultrasound. The filler material may form a permanent part of the filament, or it may be dispensable through the filament. Dispensable filler material may contain a dentifrice or other bubble promoting material. The ultrasound may be conducted, for example, through a fluid absorbing material such as a sponge that sufficiently absorbs fluid when wetted to efficiently couple the ultrasound from the transducer to the tooth surface.

Bristle filaments used in oral hygiene devices generally have a cylindrical cross-sectional configuration and are often trimmed to present a blunt exposed end surface. Devices of the present invention may employ bristle filaments having a non-cylindrical configuration that have a longer dimension along one axis than the other. Filaments having a non-circular cross-sectional configuration, such as a diamond-shaped, rectangular or oval cross-sectional configuration, may be trimmed on an angle and oriented such that the longer axis is perpendicular to the direction of bristle tip motion, thus acting as "mini-paddles" to increase fluid flow in the desired direction. Bristle filaments that are longer in one axis than the other may also be oriented with the longer axis generally perpendicular to the direction of bristle tip motion to provide a softer motion and feel, or with the longer axis generally parallel to the direction of bristle tip motion to provide a stiffer motion and feel.

Bristle filaments and tufts suitable for use with devices disclosed herein may be trimmed to promote bristle contact with the surfaces of the teeth, e.g., to promote bristle contact with both the facial and lingual tooth surfaces as well as reaching into the interproximal spaces. In devices incorporating an acoustic waveguide, bristle filaments may also be trimmed to preferentially orient the acoustic waveguide to a desired position along the surface of the teeth and/or to orient the waveguide toward a location that enhances interproximal penetration of the ultrasound.

According to one embodiment, illustrated in FIG. 5, brush head 86 incorporates a plurality of bristle tufts 93, including a combination of longer and shorter bristle tufts. Typically, bristle trim is dependent upon the orientation of the sonic bristle motion. In one embodiment, a local peak 94 of longer bristle tufts is positioned generally aligned with (as viewed from the side of the brush head) a location on acoustic waveguide 95 where the ultrasound output is maximum—generally at the longitudinal midpoint of the waveguide. When the acoustic waveguide incorporates a distal face having a peak or apex, a local peak 94 of longer bristle tufts is generally aligned with the peak of the distal waveguide face.

The tuft spacing and arrangement on brush head 86 is generally designed to promote contact of bristle tufts with tooth surfaces and to facilitate cleaning by means of the sonic oscillation and ultrasound effects. Tuft spacing is generally irregular, with tufts being arranged at a higher density in particular areas of the brush head. Preferred tuft spacing on the sides of the brush head in proximity to the side walls of acoustic waveguide 95, for example, may be less dense than the preferred tuft spacing at either end 96, 97 of the brush head in proximity to the end walls of acoustic waveguide 95 (with the waveguide 95 oriented generally along a longitudinal axis of brush head 86). In one embodiment, a relatively dense cluster of bristle tufts is provided at the distal end of the brush head 96 and another relatively dense cluster of bristle tufts is provided at the proximal end of the brush head 97, with bristle tufts arranged on either side of the longitudinal face of waveguide 95 in a less dense arrangement. Bristle tufts at either end 96, 97 of the brush head may also be stiffer than bristle tufts in a central portion of the brush head. Additionally or alternatively, tuft spacing may be arranged to create passages that allow fluid surrounding the brush head to enter the region adjacent to the brush head. In many embodiments, these passages are located near the corners of the waveguide and/or at the ends of the long axis of the waveguide. Passages 1 to 3 mm in width (space between adjacent tufts) are preferred.

The bristle tufts may be positioned and oriented to complement the action of a waveguide mounted on the brush head. In one embodiment, tufts are spaced relatively densely in proximity to the longitudinal sides of the waveguide to couple fluid to the waveguide, allowing fluid passage towards the brush head tip. The tufts, bristle filaments, waveguide and/or toothbrush head components may additionally be oriented to promote generation and transfer of bubbles having a desired size to be activated by the frequency of the applied ultrasound, i.e. bubbles whose diameter is roughly in the range from 13 to 65 micrometers. The desired orientation may depend on the surface tension, viscosity, density, and/or other property of the surrounding fluid and the wetability of the filaments, waveguide and/or other brush head components, i.e. fluids with a high surface tension and tufts and/or filaments too close to each other may prevent bubbles from forming and/or traveling towards the waveguide tip.

Bristle tufts may be oriented at an angle to perpendicular to the surface of the support plate. In one embodiment, for example, one or more bristle tuft(s) may be angled inwardly toward the waveguide at an angle of from about 1-15° to promote coupling of the fluid to the waveguide and to enhance user feel and comfort. In another embodiment, one or more tufts are oriented at an angle away from the surface of the waveguide. In another embodiment, a portion of the bristle tufts are oriented so that they're aligned generally parallel to the surface of the waveguide. The waveguide itself may be shaped to enhance this coupling, containing ridges, fins, flutes and/or other structures that may parallel the bristles. Devices of the present invention may comprise bristle tufts provided in a variety of orientations.

The bristle tufts may be arranged and/or oriented to direct the waveguide toward interproximal locations. A denser region of tufts may be provided in certain areas, for example in proximity to either end of the brush head, that tends to drop more naturally into the interproximal space. A sparser region of tufts may be provided in other areas, such as a central area of the brush head, to conform to and bend around the facial and/or lingual aspects of the teeth. Tuft positioning and orientation may also be used to prevent the waveguide from deforming and/or contacting the teeth.

Spaces between bristle tufts may be filled with another material and/or object to complement the presence of a waveguide within the brush head. This material may be open or closed cell foam, elastomeric elements/projections, or other materials that provide one or more of the following functions: effectively fill space; enhance fluid and/or bubble properties; act as a reservoir of fluid; or enhance user comfort and perception of cleaning.

The Handle Assembly and Components

An exemplary device handle housing and an exploded view of components typically mounted mounted in the handle housing is illustrated in FIG. 6. Handle 100 is generally rigid and has a generally cylindrical profile, with an internal cavity and associated internal mechanical structures for retaining the components shown. Handle 100 may also incorporate one or more user interface(s), such as on/off button 102, battery charge level indicator 104 and brush head replacement indicator 106.

A charge coil 110 and charge core 112 are generally provided in the base of the handle assembly for inductive charging from a separate charging station accessing a power supply (not shown). Charge coil 110 is electrically connected to one or more rechargeable batteries 114 that supply the power requirements for the device. Suitable rechargeable batteries include, for example, Nickel Cadmium (NiCad) batteries and NiMH (Nickel metal hydride) batteries. In the embodiment shown in FIG. 6, batteries 114 are mounted in a mechanical carrier structure 116 that provides mechanical support for the batteries and also supports a controller or circuit board assembly 118. The batteries are preferably located near the center axis of the handle assembly to provide a desirable weight balance to the handle and allow the housing to taper to a smaller size at the top and bottom. The housing may comprise an integral cylindrical component or it may be formed in one or more pieces, such as an upper and lower part, that are joined during handle assembly. This housing design allows the shape to be large in the center and taper down at the top and bottom. Different designs of the lower section may be used for different versions of the handle assembly.

In the embodiment illustrated in FIG. 6, a single circuit board is provided and all control and monitoring functions, as well as the ultrasound drive circuitry, is provided on the single circuit board. It will be appreciated that these functionalities may be provided on separate circuit boards located in separate locations within the handle, and that additional circuit boards providing additional functionality may also be provided.

It will be appreciated by those having skill in the art that ultrasound transducer drive circuits may take many forms and that various drive circuits are suitable for use in devices of the present invention. The ultrasound drive signal is typically sent from the controller to a signal conditioning and pre-amp circuit and from there is conducted to a signal amplifier. There is typically a matching network for the ultrasound transducer, which may range from quite simple to quite complex, depending upon the transducer to be matched. The purpose of the matching network is to achieve a resonance at or near that of the resonance transducer drive circuit, producing generally efficient, generally high power ultrasound acoustic output. Within certain embodiments, described in detail below, a gapped ferrite core transformer forms part of the matching network and is employed to drive the piezoelectric ultrasound transducer. "Solid-state" switches including, for example, transistors, may be employed in the ultrasound transducer drive circuitry and controlled by a microcontroller that connects the battery voltage to the primary(s) of a transformer located within the handle. Electrically efficient circuit designs frequently utilize reactive components (such as, for example, inductors and/or capacitors) in a resonant or tank circuit topology.

Exemplary ultrasound power supply (USPS) circuits may comprise one or more of the following elements: a resonant tank; resonant power; a resonant converter; a parallel resonant converter; a series resonant converter; a DC-to-AC inverter; a square wave converter; a modified sine-wave converter; and a flyback transformer. Within still further embodiments of the present invention, the USPS may employ a high voltage supply and electrical connector as a substitute for or in addition to the transformer architecture described herein. The ultrasound power supply circuit may also incorporate a high capacity capacitor to achieve an increase in battery life. Pre-charging of this capacitor while in the charger base may reduce the initial battery reliance by using the line power to supply its initial charge.

Drive motor 120 is electrically connected to the controller and incorporates a drive shaft 122 for delivering motor output, e.g. oscillation, to the device head to oscillate the toothbrush head, the acoustic waveguide and bristle tips at sonic frequencies. Drive shaft 122 typically projects from the handle assembly and is mechanically coupled to a structure in the brush head upon attachment of the brush head to the handle.

Many different types of drive motors may be used to produce oscillation at sonic frequencies in devices of the present invention. In one embodiment, a stepper motor is used to provide oscillating rotary motion of the motor drive shaft that is coupled to the toothbrush head. Stepper motors are generally controllable to provide precise manipulation of the amplitude of oscillation and toothbrush head position and may thus be suitable for use in devices in which the oscillation is varied during an operating cycle. Limited angle torque (LAT) motors may also be used as drive motors in the present invention to provide oscillating motion at an included angle of less than about 12°, preferably less than about 10°, and in yet additional embodiments at an included angle of between about 3° and 7°.

Wobble weight motors, conventional rotary motors, and piezoelectric motors or actuators may alternatively be used as drive motors for producing oscillations at sonic frequencies in devices of the present invention. In one embodiment, the motor incorporates a centering or return spring in the handle, or the portion of the motor shaft positioned in the device head assembly during operation incorporates a centering or return spring. The motor is preferably of a compact and lightweight design that fits conveniently in a generally cylindrical device handle. Preferred motor dimensions are typically between about 0.60 inch and about 1.0 inch in diameter and between about 0.5 inch and about 1.0 inch long. Pancake style motors may be employed.

Devices of the present invention may use conventional electrical or magnetic contacts to transfer power to components, such as an ultrasound transducer, that operate in the device head. In preferred embodiments, however, devices of the present invention employ a transformer to inductively couple and transfer power from the ultrasound drive circuitry and power source in the handle to the transducer assembly in the device head. The transformer assembly may additionally provide a step-up of voltage from the ultrasound power supply circuitry to the ultrasound transducer and desirably provides a physical separation of the transformer primary and secondary side components when the head assembly is detached from the handle. The transformer assembly also desirably provides electrical isolation between the power supply circuit in the handle and the ultrasound transducer circuit in the toothbrush head assembly.

Suitable transformers typically employ a primary and secondary split between the handle and toothbrush head assembly. In one embodiment, the ultrasound power supply circuit and primary side coil and core of the transformer are mounted in the device handle, and electrical contacts extend from the transformer primary coil into the main handle compartment for connection to the ultrasound power supply. As illustrated in FIG. 6, the transformer primary coil 128 and core 126 components are generally provided in a sealed enclosure in the device handle that is isolated from the other components mounted in the handle by means of sealed spacer 124 and sealed plug 130. The ultrasound transducer and secondary side coil 132 and core 134 of the transformer are mounted in the device head assembly 80 and sealed by cover 136, as illustrated in FIG. 7. The transformer assembly, in this embodiment, delivers the impedance-matched voltage required by the piezoelectric transducer to produce the desired ultrasound output intensity. The secondary coil and core, mounted in the device head, may be mounted in a stationary fashion to the housing, for example, while other portions of the device head, such as a brush head stem, remain free to oscillate. Alternatively, the secondary coil and core may be mounted in the device head for movement with other portions of the device head to achieve a moment of inertia for the toothbrush head.

The transformer coil assemblies are typically wound on a bobbin in a circular or elliptical path and sealed. Annular cores having an aperture in the center that permits the motor drive shaft to pass through the transformer assembly and couple to the toothbrush head are preferred for many applications. A small air gap (typically from about 0.010 to 0.150 inch, more typically less than 0.010 inch and, in some embodiments, between 0.040 and 0.080 inch) between the cores mounted in the handle and head is desirably maintained during operating cycles for efficient operation of the transformer. Within certain embodiments, the air gap between the cores may be achieved by using sealed coil assemblies and having the cores mounted outside these sealed assemblies. In an alternative embodiment, a ferroelectric fluid or ferro-filled elastomer may be used as a filler composition between the cores to improve transformer efficiency.

Alternative transformer designs are also contemplated. These include, without limitation, the use of torrid wound core or lamination stacks to form the core. Regardless of the precise transformer assembly adopted, it may be desirable to have the primary and secondary portions of the transformer split between the handle and toothbrush head assembly.

Within certain embodiments of the present invention, the transformer assembly used for power coupling between the device head assembly and the handle may provide power to other devices requiring power in the device head, and may further provide for the exchange of electrical information between the device head and the handle. This may, for example, be achieved by adding a coil, or an additional coil winding(s), to the primary side of the transformer assembly, or by using a center taped coil, that inductively couples signals to the coil (or coils) in the device head (i.e. the secondary side of the transformer). Thus, a signal may be sent from the handle to the toothbrush head assembly and a corresponding response provided by the toothbrush head assembly components. Alternatively, signals between the primary and secondary sides of the transformer may be coupled to induce a voltage on top of the ultrasonic drive waveform. This may, for example, provide an amplitude modulation signal riding on top of the ultrasound waveform. Alternatively, the signal frequency may be modulated to provide frequency modulation or a combination of frequency modulation and amplitude modulation.

This additional transformer component may, optionally, be employed to provide a feedback signal for monitoring transducer performance. Such feedback may, for example, control a voltage controlled oscillator (VCO) and/or a phase locked loop (PLL) for a self-tuning oscillator frequency to the transducer, to monitor operation of the ultrasound transducer at the initiation of, or during, an operating cycle or subcycle.

Devices of the present invention comprising transformers with one or more extra coil(s), or additional coil winding(s), may incorporate additional device functionality. In one embodiment, for example, the additional coil, or coil winding (s), is primarily used for interaction with the ultrasound transducer power supply circuit. In another embodiment, an additional coil, or coil winding(s), is employed to monitor the performance of the ultrasound transducer. In another embodiment, an additional coil, or coil winding(s), actuates the ultrasound transducer assembly and monitors the performance of the transducer. In yet another embodiment, an additional coil, or coil winding(s), is used for testing and/or calibration of components mounted in the handle and/or device head assembly. In still another embodiment, an additional coil and/or coil winding(s) is used to sense the environment in which the device is used, such as properties in a user's mouth and/or on a user's teeth, and communicate that information to a controller. In another embodiment, an additional coil and/or winding(s) is used to determine and/or signal the acceptable or unacceptable performance of the ultrasound transducer and/or the end of the useful life of a device head. In yet another embodiment, an extra coil and/or winding(s) may be used to monitor the transducer for a unique signature, thereby identifying a toothbrush head assembly.

Device Operating and Control Features

Devices of the present invention generally incorporate Power On and Power Off control mechanism(s) that are operable by the user. In one embodiment, a mechanical actuator is provided that, upon application of pressure, activates the device to initiate an operating cycle. Initiation of the operating cycle generally involves activation of the motor drive and/or ultrasound transducer and may incorporate a delay feature that delays initiation of the operating cycle for a predetermined period. The same mechanical actuator may be used to inactivate the device and terminate an operating cycle, or the device may be programmed to automatically shut off after termination of an operating cycle or following a predetermined delay period after termination of an operating cycle. An indication that the device has been activated may be provided by illuminating a Power On button, for example, using LEDs. In addition to Power On and/or Power Off controls, devices of the present invention may have one or more predetermined programmed operating cycles that are selectable by a user. Alternatively, devices of the present invention may be programmable by the user to provide one or more operating cycles selectable by one or more users. Devices of the present invention may additionally incorporate detection features, for example, that allow initiation of an operating cycle only when a device head is appropriately coupled to a device handle, or only when a device head is determined to be operational. In the event a non-functional device head is mounted or a device head is mounted improperly, a user interface may signal the user to make an appropriate correction.

Additional user interfaces may be provided. The level of the battery charge may be enunciated to a user, for example, by illuminating a display visible to the user using LEDs. Variations in the level of charge may be communicated and visualized, for example, by illuminating different quantities or patterns of signals. A user interface may also be provided to indicate that the device head is functioning properly, or that the device head is not functioning. Any type of user interface may be implemented including illumination of an indicator using one or more LED display(s), one or more LCD display (s), an audible tone(s), a pause or change in the operation of the drive motor, or the like. Such indicators may be incorporated variously and in different positions on the device, such as on the handle, on an accessory charging device, on a device head, or on an accessory control device.

A device head, and a device handle, may incorporate an identifier that distinguishes a head or handle from others. Such an identifier may take the form of a color or pattern coded band, light, or other identifying indicia, or may be provided as an electronic identifier detectable upon mounting of the device head in the handle, or by means of an accessory device. Multiple device heads and/or multiple types of device heads may be used with a common handle and may be distinguishable by the user and/or by the controller upon mounting of the device head on the handle. In one embodiment, a device head identifier may be associated with one or more operating protocols such that upon initiation of an operating cycle, the device identifies the device head and runs an operating protocol associated with that device head. Alternatively, if any device head is associated with more than one operating protocol, the device may prompt a user to select a protocol upon or prior to initiation of an operating cycle. The device may similarly detect different types of device heads and initiate appropriate operating cycles depending on the detection and identification of the operating head.

The device controller generally provides a timing function that separates a device operating cycle into a plurality of operating subcycles. A plurality of pre-programmed operating periods may be provided, for example, with an audible tone and/or a momentary pause or change in operating conditions producing a user-perceptible division of subcycles. In one embodiment, for example, four generally equal operating subcycles may be provided in a toothbrush of the present invention, providing convenient operation in the four brushing quadrants in the oral cavity. In another embodiment, four generally equal operating subcycles may be provided, followed by a fifth subcycle that is equal or unequal in time to the four previous subcycles. The duration of the operating cycle, for toothbrush applications, may be from about 1 min to 3 min, with operating subcycles generally having a duration of from about 10 sec-45 sec. It will be recognized that any number and combination of subcycles, periods and/or routines may be provided and may be preprogrammed in the device or may be programmable by the user. If multiple preprogrammed subcycle routines are provided, a user interface is provided to allow user selection.

In some device embodiments, the sonic and/or ultrasonic operating parameters are programmed and controlled to provide a substantially constant level of sonic and/or ultrasonic output during an operating cycle and/or during operating subcycles. In alternative embodiments, the sonic and/or ultrasonic operating parameters are programmed and controlled to provide a variable level of output or to vary certain sonic and/or ultrasonic operating parameters during an operating cycle, or during one or more operating subcycles.

For some oral hygiene applications, the oscillatory motion (bristle tip velocity, amplitude and/or frequency) is desirably greater during some periods of an operating cycle and/or an operating subcycle than at others. In some embodiments, therefore, the motor drive output producing oscillatory motion is variable over an operating cycle of the device. The motor drive and oscillatory output may, for example, operate synchronously with the ultrasound transducer and be controlled to provide higher output (greater bristle tip velocity and/or amplitude) or lower output (lesser bristle tip velocity and/or amplitude) before, during, or after the initiation or termination of an ultrasound burst. In general, when oscillatory motion is employed in combination with an ultrasound transducer and acoustic waveguide, it is preferable to vary the sonic output over an operating cycle or subcycle such that the motor drive output and oscillation is reduced during periods of ultrasound bursts and the motor drive output and oscillation is increased during periods when the ultrasound is not operating.

In one embodiment, the motor drive is controlled, for example, to reduce oscillation at sonic frequencies (bristle tip amplitude and/or velocity) during ultrasound transducer operation and to increase oscillation at sonic frequencies (bristle tip amplitude and/or velocity) when the ultrasound transducer is not operating. Thus, within certain embodiments, the timing and output of the ultrasound transducer and drive motor is synchronized. The motor drive output may be reduced by controlling one or more of the following parameters: the frequency of the motor drive output; the duty cycle of the motor drive output; the amplitude of the motor drive output; and the current supplied to the drive motor.

In another embodiment, devices of the present invention employing a drive motor are capable of determining and controlling the desired motor drive operating frequency by monitoring the resonant operating conditions of the motor. The controller may, for example, monitor both the current drawn by the drive motor and the drive frequency of the motor on a continuous or intermittent basis. The resonant frequency of the motor is detectable by monitoring the current, since the current required is lower when the motor operates at its resonant frequency. The controller may then set the drive motor operating frequency to a desired offset from the determined resonant frequency, or vary the drive motor operating frequency to achieve a desired resonant frequency under different operating conditions.

Alternatively, the motor operation may be monitored on a continuous or intermittent basis and the electromotive force (EMF) detected from the motor may be used to determine the natural resonant frequency of the motor and/or its driven system, including the brush head. Since the resonant frequency is different with and without the brush head installed, this system may be used to determine if a brush head is attached to the handle. Multiple brush heads having different inertia properties may also be detected and identified using this system, thereby identifying different users and, optionally, matching different protocols or programmed features to the different users and/or brush heads. This system may also be used in conjunction with a brush head replacement feature, to detect and identify replacement brush heads and thereby trigger a reset operation.

An accessory device may also be used, in conjunction with the controller monitoring the drive motor frequency, to monitor the angular amplitude for each frequency. The resonant frequency of the motor is detectable by monitoring the angular amplitude for each frequency. The angular amplitude measurements may be communicated to the controller, which then sets the drive motor operating frequency based on the determined resonant frequency, as above.

In some device embodiments, the ultrasound transducer is operated only as needed in certain regions of the oral cavity. It may be desirable, for example, to pulse the ultrasound only into interproximal locations and not on the lingual or facial surfaces of teeth, or vice versa. Thus, an inventive toothbrush is designed such that it can sense the interproximal location and pulse the ultrasound only when the waveguide is optimally located relative to that interproximal location. Various technologies may be employed to achieve interproximal localization. For example, a means of detection may be mechanical, e.g., by employing a spring motion to sense the three-dimensional contours of the tooth, or electrical, e.g., by detecting variances in the tooth's electrical conductivity. Preferentially the detection methodology may utilize the ultrasonic transducer as a means of sensing a force applied from the waveguide against the tooth surface. Such a force, whether intermittent or constant, may be sensed by either an electrical signal output of the transducer, a change in the acoustic impedance as viewed by the transducer/electronic circuitry, or any other similar technology available in the art. Alternatively, the ultrasound may be shut-off when the waveguide is in direct contact with the teeth and turned on when a fluid interface forms between the tooth and waveguide tip.

According to yet further embodiments, the ultrasound drive frequency is modulated, continuously or intermittently, over an ultrasound burst and/or over multiple ultrasound bursts within an operating cycle or subcycle. Continuous frequency sweeping of the ultrasound drive frequency may be provided, for example, within a predetermined frequency range and at one or more predetermined modulating frequencies. Thus, if the center frequency is Fc, the frequency may be swept from Fc−ΔF to Fc+ΔF. The rate at which the frequency is swept, Fm, is selected for desired optimum operation under operating conditions and may be variable within an operating cycle. The transducer may be operated at one or more harmonics of the resonant frequency.

Operation of an ultrasound transducer at or near its resonant frequency is preferred. Operation of the transducer using an appropriate sweep mode ensures that, under any given brushing conditions, the ultrasound module is driven at its resonant frequency for a portion of the operating time. Operation of the transducer using an appropriate sweep mode may also be used to drive ultrasound elements having varying resonant frequencies, since the sweeping action ensures the transducer will be at its resonant frequency for at least a portion of its operating cycle. This results in peak acoustic output, which typically occurs at resonance.

Modulation of the transducer drive frequency using a sweep mode, as described above, may also be implemented to adjust and improve operation of the ultrasound transducer in response to sensed environmental conditions. In one embodiment, for example, real time ultrasound drive frequency optimization is achieved by monitoring one or more characteristic(s) of the ultrasound drive circuit, such as drive current, and adjusting or tuning the drive frequency based on a comparison of the sensed current draw and a standard or desired current draw pattern or adjusted to compensate for changes in transducer parameters (e.g. transducer operating temperatures). In another embodiment, ultrasound drive frequency is swept while monitoring one or more characteristic(s) of the ultrasound drive circuit, such as drive current at the initiation of an operating cycle or following a reset command, or the like.

Within certain embodiments, devices of the present invention employ a feedback function that allows monitoring of the ultrasound transducer operation and performance at the initiation of, or during, an operating cycle or subcycle by comparison, for example, to a standard or standard ranges of transducer operating parameters. This monitoring function may be used to confirm, for example, that the device head is correctly installed and/or the ultrasound transducer element is operational. When the monitoring function indicates that the device head is not properly functioning, the controller may fail to initiate an operating cycle. Alternatively, a pacer function may be activated to prompt the user to reposition the device head. Such a pacer function may be announced to a user, for example, by means of an illuminated user interface incorporating one or more LED or LCD, by the generation of a sound, such as one or more beeps, by using a buzzer, or by pausing or changing the operation of the motor drive.

Still further embodiments of the present invention include monitoring functions that indicate the useful life and/or functionality of the ultrasound transducer element and/or device head. Exemplary feedback indicators may, for example, indicate one or more of the following: when an ultrasound system and/or device head is missing; when an ultrasound system and/or device head is present but inoperative or operating erratically; when an ultrasound system is operating but not in a desired mode of operation (e.g., out of frequency and/or an undesired mode of oscillation); and when an ultrasound system is operating normally. In one embodiment, for example, the operation of the ultrasound transducer and/or device head is monitored upon initiation of an operating cycle, and/or operable electrical connection to the ultrasound transducer is confirmed, to determine whether the device head is mounted properly.

In another embodiment, operation of the ultrasound transducer is monitored continuously or at intervals during the operating cycle or subcycle, and the sensed operating parameters are compared to one or more predetermined standards or ranges of standards to determine whether the ultrasound transducer and/or device head is operating within acceptable ranges. A user interface indicating normal operation may be activated when the device head and/or ultrasound transducer is operating within acceptable ranges. Upon detection of unacceptable operating during or at initiation of an operating cycle, a user interface may be activated to advise the user of the malfunction or advise the user to replace the device head.

Detection of unacceptable transducer or device head function may be monitored, for example, by monitoring the current drawn by the ultrasound power supply circuit and ultrasound transducer. An ultrasound transducer or device head that is not functioning properly exhibits a different current signature than one that is functioning properly. The current signature of a functioning transducer in "normal" use, for example, is characterized by sudden variations in the current. The current signature of a non-functioning device head (in which the waveguide has delaminated, for example, or electrical contact is not being made with the transducer) is characterized by constant current that doesn't exhibit substantial variation. In one control scheme, therefore, a running current "delta" (min-max) is acquired during each operating cycle or subcycle. If the min-max delta detected over the operating cycle or subcycle is large, the brush head is functioning properly. If the min-max delta detected over the operating cycle or subcycle is small, one or more failures have occurred and an appropriate user interface is activated.

Within yet further embodiments, the controller may be programmed to count the number of device operating cycles. The number of operating cycles for a particular device head may be displayed in a user interface. The controller may also be programmed to count the number of operating cycles and to monitor the functionality of the device head simultaneously. Following a predetermined number of uses (typically 2 uses per day for 6 months or 180 uses), the microprocessor is set to monitor the electrical current flowing through a current sense element located in the handle and detect unacceptable device head operation, as described above. In yet another embodiment, the controller may be programmed to monitor the function of the device head at predetermined intervals, e.g., following a predetermined number of device head operations or activations. For example, the controller may be programmed to monitor twenty consecutive device head uses and make an assessment of how many different device heads are being used with that handle. Depending on the pattern of uses and proportion of "good" to "bad" responses during an operating cycle or subcycle, or the proportion of "good" to "bad" operating cycles or subcycles, the microprocessor may be programmed to activate a user interface.

Certain reset functions may be programmed in the controller and initiated by a user through a user interface. Following replacement of a defective device head, for example, a user may provide input to a user interface on the device or an accessory unit and effectively reset the controller and its device head detection, counting and/or monitoring functions. The reset function may instruct the controller to initiate a new monitoring and control cycle that may be the same as or different from a previous monitoring and control cycle. It will be appreciated that many different monitoring and control algorithms may be programmed into the controller.

Alternatively, separate test protocols may be implemented to monitor the performance of a device assembly. In one such test protocol, the device head and ultrasound transducer may be immersed in a vessel containing an embedded transducer sense element. The vessel may, for example, be filled with water and the ultrasound signal transmitted by the toothbrush head detected by the sense element and the acoustic output measured by a system within the vessel. The strength of the signal may be converted to a signal to the user that indicates the performance of the ultrasound element. Within various embodiments of the present invention, the test vessel may be provided as a stand-alone unit or may be incorporated into an accessory device charger or control unit.

Within other embodiments of the present invention, toothbrushes may employ one or more mechanisms, including bactericidal ultrasound-based mechanisms, to achieve the antimicrobial treatment of the toothbrush head thereby reducing the level of live bacteria remaining within the toothbrush elements.

Adaptive Feedback Mechanisms

Within certain embodiments, toothbrushes of the present invention comprise electronic circuitry that permits both the transmission and detection of ultrasonic signals for real-time modulation of ultrasound characteristics to achieve enhanced bubble oscillation and, hence, dental plaque removal. Transmission characteristics are monitored electronically and the resulting feedback is fed into a detection circuit and/or microprocessor. The individual characteristics of the ultrasound protocol (such as, for example, PRF, CPS, duty cycle, Mechanical Index factors, etc.) and/or sonic motor drive parameters (such as, for example, drive voltage, frequency, duty cycle, pulse width, etc.) can be modified to permit improved ultrasonic output for improved plaque removal. Such "smart ultrasonic" power toothbrushes optimize bubble size and density to produce superior plaque removal as compared to a fixed drive ultrasonic transducer and sonic motor.

Ultrasound does not travel efficiently through air. It does, however, transmit quite efficiently in aqueous environments, so long as the ultrasonic transducer is designed to emit in an aqueous (water) medium. As discussed above in reference to microbubbles, acoustic streaming, and acoustic microstreaming, when bubbles are encountered in a relatively small bubble population (i.e. 1% to 20%) and when their size matches the ultrasound transducer drive frequency, the bubbles are excited to vibrate and this increases the cleaning effect compared to the cleaning provided by a convention, sonic motor driven toothbrush. When ultrasound is used in combination with sonic frequencies, the ultrasound waves become attenuated when the bubble size and population is too large. This phenomenon is characterized by a large void fraction (e.g., more than 30% void fraction or trapped air bubbles). When the sonic parameters are held constant, the void fraction primarily depends upon fluid properties. Furthermore, void fraction is significantly higher in a dentifrice medium than in water. Thus, the capacity of "smart" ultrasonic power toothbrushes of the present invention to control bubble characteristics and/or to control operation of the device to take advantage of the operating (fluid) environment is of significant benefit to plaque removal efficacy. Several different protocols are described below and may be used to detect and control bubble characteristics and modulate operating parameters during operation of a device of the present invention.

Process A—A transmit transducer emits ultrasound into the bubbly fluid and a receiver transducer detects ultrasound scattering and variation. Big bubbles or dense populations of bubbles are more reflective and tend to scatter the ultrasound. The receiver transducer provides input to a detection circuit and/or microprocessor based algorithm, which is capable of detecting and defining the fluid acoustic properties of the operating environment based on the detected ultrasound scattering and variation. Based on the determined fluid properties, the sonic drive motor and/or the ultrasound protocol is adjusted automatically and optimized for the fluid properties detected in the operating environment.

Process B—Following the emission of ultrasound transmit signals, ultrasound reflections are detected by the same transducer, or by another separate (receive) transducer. The received reflection signals are input to the microprocessor, which detects and defines the acoustic properties of the fluid operating environment based on the ultrasound reflections. The controller may then adjust either the sonic motor frequency or duty cycle, or the ultrasound operating parameters, to "tune" the operation of the device to the fluid operating environment.

It should be noted that there are several conditions that provide distinct differences in operation and performance of the waveguide. When the waveguide is fully immersed in water, ultrasound is emitted in a low impedance environment and easily exits the waveguide. When the operating environment has a higher impedance as a result, for example, of the presence of air or large population(s) of bubbles, the ultrasound is emitted in a higher impedance environment and exits the waveguide differently. This effect can be detected and input to the microprocessor for control of sonic motor or ultrasound protocol(s).

Process C—The same transducer may be used for both ultrasound transmit and ultrasound Receive functions. Echo ultrasound data is collected between Pulse Repetition Frequency (PRF) bursts and analyzed to detect changes in reflection due to bubble population and size. Motor speed and/or ultrasound burst length and/or PRF may be adjusted during use based on features extracted from this reflected signal.

Process D—Forward and reverse power, impedance or other characteristics of variance delivered to the transducer are monitored. The bubbly fluid characteristics change the coupling of ultrasound into the fluid. Increasing reverse power indicates decreasing coupling under these conditions, and the motor speed and/or ultrasound burst length and/or PRF maybe adjusted to decrease the reverse power. Sense turns on the matching transformer can reflect magnetic flux variations which represent variations in the transducer load, which can then be decoded through a microprocessor algorithm to assess the transducer life condition. Various enunciators (sound, light, brush motion, oscillation, musical note, etc.) can then be engaged to advise an operator to replace the brush head or transducer element.

All of the processes disclosed herein above comprise the step of monitoring conditions within the toothbrush, circuit, and/or user's mouth. Monitoring signals may be routed to a comparative or computing device, such as a microprocessor, differential amplifier, and/or A-D converter, to detect electrical changes and convert them into control modifications affecting: (1) the ultrasonic protocol (i.e. voltage, frequency, burst conditions, etc.) which defines the transducer output and (2) the sonic protocol (i.e. motor drive voltage, current, duty cycle, pulse width, etc.) that defines the motor characteristics controlling the sonic brushing characteristics (i.e. bristle tip velocity, acceleration, and/or cavitation within the dental slurry).

Fluid characteristics may also be controlled by modulating the sonic and/or ultrasonic operating protocol(s) (i.e. viscosity, bubble size, bubble density, color, etc.). The amount and location of fluid in the operating environment may be modified by introducing fluid or withdrawing fluid from the operating environment. Fluid present in the operating environment, e.g. the oral cavity, may be withdrawn to a reservoir when it is in excess, and additional fluid may be introduced when the fluid quantity is insufficient or to modify the fluid properties, thereby enhancing the ultrasonic effects.

In those embodiments of the present invention wherein the toothbrush head is equipped with a mechanism to dispense a powder or some other material that alters the bubble forming properties of the dental fluid, the feedback and controls previously disclosed may be employed as well. For example, dispensing baking soda will modify the pH of the dental fluid, dispensing other additives can reduce surface tension and reduce excessive bubbling effects of the surfactants commonly found in toothpaste.

The control and/or dispensing of a topical fluid or powder, when combined with the ultrasound, enhances cleaning, stain removal, and whitening, and changes the properties of the dental fluid to result in improved in dental cleaning and general oral health (i.e. reduced gingivitis, toughened gums, reduced carries, plaque, bad breath, dry mouth, etc.).

The toothbrush sensor and controls described above may be employed in order to control the angular position of a stepper motor (potentially 360 degree rotation). The motor, once in a new position, will resume its oscillating brushing motion. This type of control of toothbrush head movement allows the toothbrush head to move to a position in which it senses the interface of soft and hard tissue (gums and teeth). When air is detected, the toothbrush head position is redirected to a position where the tooth gum interface is again present. Such an embodiment reduces user control of the toothbrush head such that the toothbrush head automatically tracks to the optimal brushing position.

Alternative or additional technologies that may be employed to achieve a suitable feedback function that may be used in toothbrushes of the present invention include, but are not limited to light-emitting diodes, photodiodes, phototransistors, and/or opto-couplers that sense light beam attenuation. Since light can pass through air bubbles with only some refraction, the light transmission may not be directly proportional to acoustic transmission. Ultrasonic transmission will either be reflected or absorbed by a bubble population, which will be at different wavelengths than light sources. An opto-coupler, however, installed in a toothbrush head, typically within the acoustic waveguide, sends light across a notch in the waveguide and is received on the other side of the notch. The fluid density, according to the light transmission, is representative of the fluid presence and condition in the direct vicinity of the waveguide. Light may be transmitted into or from the nylon bristles and variations in transmission detected that are correlative of fluid properties. These variations can then be fed into a microprocessor algorithm to aid in control of the sonic and ultrasonic protocols similar to the other methods described herein. Still further embodiments of the present invention exploit the beneficial microbiological effects, especially when coupled with the other ultrasound and sonic protocols.

Brushing power may also be adjusted based on how hard the user is pressing against the teeth. The force applied may be determined by employing load sensing transducers and/or by measuring the current through the motor. Depending upon the force applied, the power applied to the motor may be reduced to reduce the risk of abrasion from too much mechanical scrubbing. Alternatively or additionally, the brush may be operated in an optimized mode using the feedback signal by continuously adjusting the sonic drive power level based on the feedback.

Design, Shape, and Features of Exemplary Toothbrushes

The general shape and size of oral hygiene devices of the present invention having a handle and a device head, take into account both ergonomic functionality and aesthetic appearance. Two distinct grip areas may be provided that differ in size and positioning, and are designed for different tasks. One grip section is for general handling (i.e. transfer into and out of a charger and holding by the user while applying dentifrice). This grip section is generally grasped by a full grip in the palm of the hand. This area is located in the middle and lower portion of the device handle and has a generally oval or elliptical cross sectional configuration. A second grip area is located in the upper portion of the toothbrush handle and is optimized for holding the device while operating it (e.g., brushing the teeth). This grip section is generally grasped with the finger tips and may employ a surface texture and/or a soft material to help prevent slipping in the hand. The on/off switch is generally located at the interface between the upper grip area and the device head. The on/off switch may be provided as a mechanical switch activated, for example, by modest pressure.

Devices of the present invention may have a general configuration and profile having a larger section in the middle, tapering to smaller sections near the top and bottom. An oval, elliptical, or triangular cross sectional shape typically feels smaller in the hand and is easier for small hands to grasp. An oval shaped toothbrush handle may be advantageous in those applications in which it is important to determine, by feel, the orientation of the toothbrush head.

Features and shape of the grip areas may be employed to achieve one or more of the following functionalities: (a) an aid in determining proper orientation of the brush bristles; (b) the shape at a handle to toothbrush head interface may provide a visual aid for proper alignment; (c) the general shape may communicate product functions and/or technology such as a sonic wave and/or bubbles; (d) a power (on/off) switch may be located above the upper grip area; (e) a display (e.g., battery charge indication) may be located near the center of the handle.

Fluid Control and Fluid Dispensing

Fluid is required at the tip of the waveguide to couple ultrasound emanating from the waveguide tip to the oral cavity and tooth surfaces. Absent the addition of significant fluid to the oral cavity at the beginning of an operating cycle, the availability of fluid may vary from the beginning of the operating cycle to the end. Typically, saliva is generated by the user at a rate of approximately 2 ml/min. Dentifrice, which is typically applied to the device as a paste and/or gel at the beginning of an operating cycle, breaks down and integrates within the saliva and/or water added to form the dental slurry. As a result of the nature of the dentifrice and variation of fluid availability, the dental slurry may be relatively thick at the beginning of a brushing event and relatively thin at the end. To reduce the variation of fluid availability and composition during an operating cycle, the device may incorporate a component that (a) introduces fluid at the beginning of an operating cycle, (b) withdraws fluid toward the end of an operating cycle, or (c) both introduces and withdraws fluid during an operating cycle. The addition and/or withdrawal of fluid may be either active (e.g., by providing a pump and/or vacuum mechanism) or passive (e.g., by providing fluid absorbing material in proximity to Is the brush head and oral cavity environment).

During a typical operating cycle, fluid naturally migrates to the bottom of the oral cavity, surrounding the lower (mandibular) teeth. Less fluid surrounds the upper (maxillary) teeth. It is desirable to carry fluid with the brush head and provide it such that it is available to couple between the waveguide and the teeth, both while brushing the lower and upper teeth. The toothbrush head may, additionally, provide a component that absorbs or collects fluid during brushing the upper teeth dispenses or emits fluid (the same and/or replacement fluid). This addition or subtraction of fluid may be active (e.g., pump/vacuum) or passive (e.g., fluid absorbing material).

Within certain embodiments, oral hygiene devices of the present invention may further employ a mechanism for dispensing fluid and/or other media (including, but not limited to water, pre-formed bubbles, a paste, a gel, and/or a powder), thereby enhancing the performance of the device. For example, it may be advantageous to improve the acoustic properties of the fluid in the mouth and/or induce a chemical or physical reaction by application of the ultrasound. Typically, a reservoir of fluid (or other media) is provided in the toothbrush head assembly, or in the handle assembly with passages for moving fluid from a remote reservoir to a dispensing area at the device head. A pump or flow control valve may be used to dispense the fluid from the reservoir.

The fluid may exit the toothbrush head through the acoustic waveguide and/or through a port or valve or nozzle in the area of the bristles. In some embodiments, the pumping action or actuation of a flow control valve may be produced by the transducer element contained within the toothbrush head. Alternatively, an electromechanical device may be provided in the toothbrush head assembly to facilitate pumping action or flow control. Electrical coupling of the dispensing device within the toothbrush head assembly may be achieved with a control circuit in the handle assembly that is provided through the transformer assembly.

Alternative embodiments of the present invention provide a small length of filament from the wave guide (or bristle area) that aids in the transmission of the ultrasound and/or action of the bristles. As the filament wears, an additional amount (small length) is dispensed from the toothbrush head to maintain the placement of an optimal length.

Still further embodiments of the fluid storage devices used in combination with the toothbrushes of the present invention include a sponge that stores fluid when full and releases fluid when squeezed thereby increasing the amount of fluid in the mouth. The squeezing force on the sponge may be achieved by the ultrasound transducer and/or other electromechanical device within the toothbrush head. When filled, the sponge is also an effective medium for transmitting ultrasound and, thereby, performs in a manner similar to an acoustic waveguide, as described herein above.

Regardless of the precise reservoir configuration, it will be appreciated that the amount of stored fluid (or other media) may depend upon the specific function contemplated. If a large volume of fluid is to be dispensed during brushing, then a mechanism for refilling the reservoir may be employed. Thus, a reservoir may be adapted to permit refilling prior to each use or, alternatively, the reservoir may hold sufficient fluid to permit several brushings. If only a very small volume of fluid is needed for brushing, then a reservoir in the toothbrush head assembly may contain sufficient fluid to last the life of the toothbrush head assembly. The latter option may be further exploited in order to determine the end of the useful life of a toothbrush head assembly.

In those embodiments wherein a fluid reservoir is attached to and/or contained within a toothbrush handle assembly, a fluid path carries the fluid from the reservoir to the brush head. This fluid path may be a flexible tube and/or may be routed through the motor shaft into a hollow bush neck to the bristle area of the toothbrush head. A pump or flow control valve may, for example, be located in either the toothbrush head assembly or the handle. The pump or flow control valve may, alternatively, be actuated directly by the user (a mechanical pump or valve) or may be controlled (electrically) by the handle electronics.

Thus, depending upon the precise toothbrush configuration contemplated, the fluid dispensing system may comprise one or more specific characteristics and/or attributes including, but not limited to, (a) fluid dispensed through the acoustic waveguide; (b) motion from the ultrasound transducer may be used to provide a pumping action; (c) a pressurized reservoir may employ the ultrasound transducer to actuate a flow control valve; (d) fluid may travel from a handle through a drive shaft to a toothbrush head; (e) fluid may be contained within the toothbrush head assembly; (f) fluid may be used to alter the acoustic properties of fluid in a user's mouth; (g) fluid may interact with ultrasound to improve efficiency of the toothbrush; (h) fluid may be used to add to fluid in mouth in order to ensure sufficient volume of fluid in mouth; (i) dispensing of fluid may be based on acoustic properties in a user's mouth as measured by an ultrasound transducer; (j) a fluid supply in a toothbrush head assembly may be sufficient to last the life of the toothbrush head thereby obviating the need for refilling and enabling its use to indicate end of a toothbrush head's useful life; (k) a change in taste of a stored fluid may be employed to indicate end of a toothbrush head's useful life; (l)

dispensing a gel, paste or powder in place of fluid; (m) dispensing a filament or other stranded material that acts as an acoustic waveguide and/or similar device to transmit ultrasound; (n) dispensing a fluid and/or other media to coat the teeth prior to brushing; (o) dispensing a fluid, such as fluoride, to enhance after-brushing protection; and (p) synchronizing fluid dispensing, ultrasonic burst, and brush motion/positions.

Dentifrice Design and Compositions

Within certain related embodiments, it is contemplated to provide a dentifrice that is particularly suitable for use with the inventive power toothbrush described herein. For example, it is herein contemplated that such a dentifrice will facilitate the creation of a desirable bubble population that may be acted upon by the ultrasonic transducer and acoustic waveguide disclosed herein.

The natural bubble population within a dental fluid may be assayed by the tendency of that fluid to absorb ultrasonic energy that is transmitted through it. The higher the absorption, the more bubbles that are present at the relevant size (given heuristically by the resonance formula, developed originally for bubbles in pure water at 37 degrees Celsius, although applicable as an approximation for more general conditions $F_0R_0=3.26$, where the frequency $F_0$ is given in MHz and the radius $R_0$ of the bubble is given in microns), although many bubbles off-resonance would also create desired plaque and stain removal effects.

Typically, for example, dentifrices according to the present invention facilitate the formation of bubbles within the dental fluid having a diameter of between about 1 µm and about 150 µm that resonate when ultrasound is applied in the 20 kHz to 3 MHz frequency range. More typically, dentifrices according to the present invention facilitate the formation of bubbles within the dental fluid having a diameter of between about 1 µm and about 100 µm that resonate when ultrasound is applied in the 30 kHz to 3 MHz frequency range. Still more typically, dentifrices according to the present invention facilitate the formation of bubbles within the dental fluid having a diameter of between about 5 µm and about 30 µm that resonate when ultrasound is applied in the 100 kHz to 600 kHz frequency range. In an exemplary dentifrice presented herein, bubbles are formed in the dental fluid that have a diameter of between about 12 µm and about 26 µm that resonate when ultrasound is applied to those bubbles with an ultrasound transducer operating in the 250 kHz to 500 kHz range.

Dentifrices suitable for use with the toothbrushes disclosed herein comprise a surfactant that produces surface tension values that facilitate production and stabilization of bubbles in a suitable size range for stimulation by the ultrasonic transducer in combination with an acoustic waveguide. Typically, surfactants employed in the dentifrices disclosed herein produce surface tensions in the range of about 0.1 Pa to about 500 Pa, more typically in the range of about 0.2 Pa to 250 Pa, and still more typically in the range of about 0.5 Pa to about 50 Pa.

Alternatively, or in addition to providing a dentifrice as described above that promotes bubble formation, bubbles having a desired size range may be incorporated in a dentifrice or another composition and introduced directly into the oral cavity by application of the composition on a toothbrush or by introduction of the composition into the oral cavity. Bubbles having a diameter of between about 1 µm and about 150 µm, more typically between about 1 µm and about 100 µm, in some embodiments between about 5 µm and about 30 µm, and in yet other embodiments between about 12 µm and about 26 µm may be incorporated directly in a dentifrice composition or in another composition, such as a mouthwash or another generally liquid, gel-like or semi-solid carrier for delivery to the oral cavity.

Bubbles in the carrier material may be present as voids in the composition itself, or as microspheres or other microstructures forming gas-filled voids in the carrier material. The OPTISON™ ultrasound contrast enhancing composition, for example, comprises a suspension of microspheres having a mean diameter of 2.0-4.5 µm, the microspheres being formed from human serum albumin and being filled with an octafluoropropane gas. A population of microspheres of the desired size range (as described above), formed using a material that's safe for human consumption and generally inert and filled with a gas that's safe for human consumption and generally inert may be incorporated in a suitable carrier material and used, in conjunction with toothbrushes of the present invention, to promote effective cleaning.

All references to ranges of parameters described in this specification are understood to include reference to a range equal to and greater than the lower value of each range, as well as ranges equal to and less than the higher value of each range. Thus, for example, the recitation of a carrier frequency of between about 250 and about 500 kHz in this specification is interpreted to include carrier frequencies of 250 kHz and greater; carrier frequencies of 500 kHz and less; as well as carrier frequencies within the stated range.

It will be appreciated that the combination of an acoustic waveguide with an ultrasound transducer and/or motor generating acoustic energy at sonic frequencies may be used in other types of oral hygiene devices and, indeed, in other types of devices for cleaning surfaces, and the inventions described herein are not limited to toothbrush embodiments, which are described in detail.

All U.S. and foreign patents and patent applications, and all other references, are hereby incorporated by reference in their entireties.

We claim:

1. An oral hygiene device comprising: a device head support structure having an acoustic waveguide and at least one bristle tuft composed of a plurality of bristles projecting from the support structure; and an ultrasound transducer acoustically coupled to the acoustic waveguide that operates to produce ultrasonic energy at frequencies of less than 1.5 MHz during an operating cycle, wherein the acoustic waveguide is mounted to and contacts an upper surface of the transducer and at least a portion of side walls of the transducer.

2. The oral hygiene device of claim 1, wherein the ultrasound transducer operates to produce a peak negative acoustic pressure of from 0.1-1 MPa during an operating cycle.

3. The oral hygiene device of claim 1, wherein the ultrasound transducer operates to produce ultrasonic energy at frequencies of less than 500 KHz during an operating cycle.

4. The oral hygiene device of claim 1, additionally comprising a motor that operates, during an operating cycle, to produce an oscillating motion at the device head support structure.

5. The oral hygiene device of claim 4, wherein the motor operates to oscillate the tips of the bristles at a peak velocity of less than 1.5 m/sec during an operating cycle.

6. The oral hygiene device of claim 1, additionally comprising an ultrasound drive circuit electrically coupled to the ultrasound transducer, wherein the ultrasound drive circuit is controlled by a circuit board.

7. The oral hygiene device of claim 1, wherein the device operates to produce shear stresses of from about 1 Pa to about 30 Pa in dental fluids during an operating cycle.

8. The oral hygiene device of claim 1, additionally comprising a handle attachable to the device head support structure, a rechargeable power supply provided in the handle, and a battery charging station connectable to an external power supply for recharging the rechargeable power supply.

9. The oral hygiene device of claim 1, additionally comprising a monitoring feature that monitors the useful life of the ultrasound transducer and provides an indication when the ultrasound transducer exhibits unacceptable function.

10. The oral hygiene device of claim 1, wherein operation of the ultrasound transducer is monitored during operating cycles to sense at least one operating parameter and at least one sensed operating parameter is compared to at least one predetermined standard to determine whether the ultrasound transducer exhibits unacceptable function.

11. The oral hygiene device of claim 1, additionally comprising a user interface indicating normal operation when the ultrasound transducer exhibits acceptable function.

12. The oral hygiene device of claim 1, additionally comprising a user interface advising a user to replace the device head upon detection of unacceptable function of the ultrasound transducer.

13. The oral hygiene device of claim 1, additionally comprising a monitoring feature programmed to count the number of device operating cycles.

14. The oral hygiene device of claim 1, wherein the ultrasound transducer produces ultrasound energy having different frequencies during an operating cycle.

15. The oral hygiene device of claim 14, wherein the ultrasound drive frequency is swept within a predetermined frequency range during an operating cycle.

16. An oral hygiene device comprising: a device head having an acoustic waveguide and at least one bristle tuft comprising a plurality of bristles projecting from a support structure; an ultrasound transducer mounted in the device head and acoustically coupled to the acoustic waveguide that operates, during an operating cycle, to produce ultrasonic energy at frequencies of less than 1.5 MHz; a power source; and a transformer assembly that inductively couples and transfers power from the power source to the ultrasound transducer.

17. The oral hygiene device of claim 16, wherein the ultrasound transducer produces a peak negative acoustic pressure of from 0.1-1 MPa during an operating cycle.

18. The oral hygiene device of claim 16, additionally comprising a motor that operates, during an operating cycle, to produce an oscillating motion at the device head.

19. The oral hygiene device of claim 18, wherein the motor operates to oscillate the tips of the bristles at a peak velocity of less than 1.5 m/sec during an operating cycle.

20. The oral hygiene device of claim 16, wherein the acoustic waveguide is provided as a unitary structure having a generally block-like, three-dimensional configuration and having multiple faces, and the ultrasound transducer operates to produce ultrasonic energy at frequencies of less than 1.0 MHz during an operating cycle.

21. The oral hygiene device of claim 16, additionally comprising a handle attachable to the device head support structure, a rechargeable power supply provided in the handle, and a battery charging station connectable to an external power supply for recharging the rechargeable power supply.

22. The oral hygiene device of claim 16, additionally comprising a transformer primary side coil and core coupled to the power source and a transformer secondary side coil and core coupled to the ultrasound transducer.

23. The oral hygiene device of claim 16, wherein the power source is mounted in a device handle and the transformer assembly provides for the exchange of electrical information between the device head and the device handle.

24. The oral hygiene device of claim 16, additionally comprising a user interface advising a user to replace the device head upon detection of unacceptable function of the ultrasound transducer.

25. The oral hygiene device of claim 16, additionally comprising a monitoring feature that monitors the useful life of the ultrasound transducer and provides an indication when the ultrasound transducer exhibits unacceptable function.

26. The oral hygiene device of claim 16, additionally comprising a monitoring feature programmed to count the number of device operating cycles.

27. An oral hygiene device comprising an acoustic waveguide and at least one bristle tuft projecting from a device head support structure, an ultrasound transducer assembly acoustically coupled to the acoustic waveguide that operates to produce ultrasonic energy at frequencies of greater than about 20 kHz during an operating cycle, and an ultrasound drive circuit coupled to the ultrasound transducer assembly, wherein the ultrasound transducer assembly comprises at least two piezoelectric elements arranged mechanically in series, with each piezoelectric element being electrically connected to another piezoelectric element in parallel.

28. The oral hygiene device of claim 27, wherein each piezoelectric element has electrically conductive material associated with one or more of its surfaces.

29. The oral hygiene device of claim 27, wherein the acoustic waveguide is mounted to and contacts at least an upper surface of the transducer.

30. The oral hygiene device of claim 27, wherein the ultrasound transducer produces a peak negative acoustic pressure of from 0.1-1 MPa during an operating cycle.

31. The oral hygiene device of claim 27, additionally comprising a motor that operates, during an operating cycle, to produce an oscillating motion at the device head support structure.

32. The oral hygiene device of claim 27, additionally comprising a handle attachable to the device head support structure, a rechargeable power supply provided in the handle, and a battery charging station connectable to an external power supply for recharging the rechargeable power supply.

33. The oral hygiene device of claim 27, additionally comprising a user interface advising a user to replace the device head upon detection of unacceptable function of the ultrasound transducer.

34. The oral hygiene device of claim 27, additionally comprising a monitoring feature programmed to count the number of device operating cycles.

* * * * *